US008311299B2

(12) United States Patent
Qian et al.

(10) Patent No.: US 8,311,299 B2
(45) Date of Patent: Nov. 13, 2012

(54) METHOD AND SYSTEM FOR INTELLIGENT QUALITATIVE AND QUANTITATIVE ANALYSIS OF DIGITAL RADIOGRAPHY SOFTCOPY READING

(75) Inventors: Jianzhong Qian, Princeton Junction, NJ (US); Li Fan, Belle Mead, NJ (US); Guo-Qing Wei, Plainsboro, NJ (US); Cheng-Chung Liang, West Windsor, NJ (US)

(73) Assignee: Edda Technology, Inc., Princeton Junction, NJ (US)

( * ) Notice: Subject to any disclaimer, the term of this patent is extended or adjusted under 35 U.S.C. 154(b) by 106 days.

(21) Appl. No.: 12/407,335

(22) Filed: Mar. 19, 2009

(65) Prior Publication Data

US 2009/0221881 A1   Sep. 3, 2009

Related U.S. Application Data

(62) Division of application No. 11/024,033, filed on Dec. 29, 2004.

(60) Provisional application No. 60/537,558, filed on Jan. 21, 2004, provisional application No. 60/562,260, filed on Apr. 15, 2004.

(51) Int. Cl.
*G06K 9/00* (2006.01)
(52) U.S. Cl. ........ 382/128; 382/130; 382/131; 600/407; 600/408
(58) Field of Classification Search .................. 382/128, 382/132; 600/408
See application file for complete search history.

(56) References Cited

U.S. PATENT DOCUMENTS

| 5,010,889 | A | 4/1991 | Bredesen et al. | |
|---|---|---|---|---|
| 5,622,171 | A | 4/1997 | Asada et al. | |
| 5,987,094 | A | 11/1999 | Clarke et al. | |
| 6,149,585 | A | 11/2000 | Gray | |
| 6,678,703 | B2 | 1/2004 | Rothschild et al. | |
| 6,690,816 | B2 * | 2/2004 | Aylward et al. | 382/128 |
| 6,836,558 | B2 | 12/2004 | Doi et al. | |
| 6,941,323 | B1 * | 9/2005 | Galperin | 1/1 |
| 7,274,810 | B2 * | 9/2007 | Reeves et al. | 382/128 |
| 7,483,919 | B2 * | 1/2009 | Galperin | 1/1 |
| 7,545,965 | B2 * | 6/2009 | Suzuki et al. | 382/128 |
| 7,764,282 | B2 * | 7/2010 | Chiba | 345/419 |
| 7,876,319 | B2 * | 1/2011 | Chiba | 345/419 |
| 2002/0021828 | A1 | 2/2002 | Papier | |
| 2003/0026503 | A1 | 2/2003 | Kallergi et al. | |
| 2003/0156762 | A1 | 8/2003 | August | |
| 2003/0161513 | A1 | 8/2003 | Drukker | |
| 2004/0062427 | A1 | 4/2004 | Biswas | |

(Continued)

OTHER PUBLICATIONS

United States Office Action issued in U.S. Appl. No. 11/024,033 dated Jan. 26, 2010.

(Continued)

*Primary Examiner* — Tse Chen
*Assistant Examiner* — Baisakhi Roy
(74) *Attorney, Agent, or Firm* — SNR Denton US LLP

(57) ABSTRACT

The present invention describes a method and system for intelligent diagnostic relevant information processing and analysis. Information associated with a patient is processed via an image reading platform. Based on such processed information, a matrix of diagnosis decisions containing diagnostic related information is generated via a matrix of diagnosis decision platform. A diagnostic decision is made based on the diagnostic relevant information. The image reading platform and/or the matrix of diagnosis decision platform encapsulate information and toolkits to be used to manipulate the information.

28 Claims, 25 Drawing Sheets

U.S. PATENT DOCUMENTS

2004/0252870 A1* 12/2004 Reeves et al. .............. 382/128
2006/0262117 A1* 11/2006 Chiba ..................... 345/440
2010/0231584 A1* 9/2010 Chiba ..................... 345/419

OTHER PUBLICATIONS

International Preliminary Report on Patentability and Written Opinion of the International Searching Authority issued in International Application No. PCT/US05/00118, dated May 10, 2007.

International Preliminary Report on Patentability and Written Opinion of the International Searching Authority, issued in corresponding International Patent Application No. PCT/US2005/000118, dated on Jun. 28, 2007.

Canadian Office Action issued in Canadian Patent Application No. CA 2,554,162, mailed Jan. 27, 2009.

United States Office Action issued in U.S. Appl. No. 11/038,491, dated Sep. 28, 2009.

Taiwanese Search Report dated Apr. 18, 2011 corresponding to Taiwanese Serial No. 094100341.

Chinese Office Action corresponding to Chinese Serial No. 200580002905.1 dated Dec. 12, 2011.

* cited by examiner

METHOD AND SYSTEM FOR INTELLIGENT QUALITATIVE AND QUANTITATIVE ANALYSIS OF DIGITAL RADIOGRAPHY SOFTCOPY READING

CROSS-REFERENCE TO RELATED APPLICATIONS

The current Application is a Divisional of U.S. application Ser. No. 11/024,033 filed Dec. 29, 2004, claiming priority of U.S. Provisional Application No. 60/537,558 filed Jan. 21, 2004, and U.S. Provisional Application No. 60/562,260 filed Apr. 15, 2004, the entire contents of which applications are herby incorporated by reference.

BACKGROUND OF THE INVENTION

1. Field of the Invention

The invention disclosed herein relates to a system and method for assisted medicine. Particularly, it relates to diagnostic information analysis.

2. Description of Related Art

Most radiographic images are complex due to the fact that three dimensional anatomical structures are projected on a two dimensional image plane. For example on chest radiographic images, over 60 percent of the lung region may be occluded by ribs. Object(s) of interest such as nodules may therefore overlap with anatomical structures such as ribs, reside in shadows, or may be occluded by other types of objects. These may cause difficulty to observe the object(s) of interest and discern the boundary of such object(s). Existing systems have some shared shortcomings or weaknesses in assisting and facilitating physicians' softcopy reading of digital/digitized radiographic images. First, most of the existing systems are not capable of providing quantitative measurements, which are often used by physicians to reach a diagnostic decision. This incapability is often related to the difficulties in segmenting out nodules and/or lesions in images when structural/anatomic noise exists due to, for example, the difficulties stated above. Second, existing systems are not capable of complying with an existing clinical workflow and provide only assistance in certain stages of such a workflow. Third, existing systems usually employ black-box approaches so that it is not possible for physicians to interact in real time with such systems. As a consequence, such systems can provide only assistance based on prior knowledge that is built in the system rather than offering assistance based on physician-specific knowledge and experience.

BRIEF DESCRIPTION OF THE DRAWINGS

The present invention is further described in terms of exemplary embodiments, which will be described in detail with reference to the drawings. These drawings are non-limiting exemplary embodiments, in which like reference numerals represent similar parts throughout the several views of the drawings, and wherein.

DETAILED DESCRIPTION OF A PREFERRED EMBODIMENT OF THE INVENTION

Figure 1A:
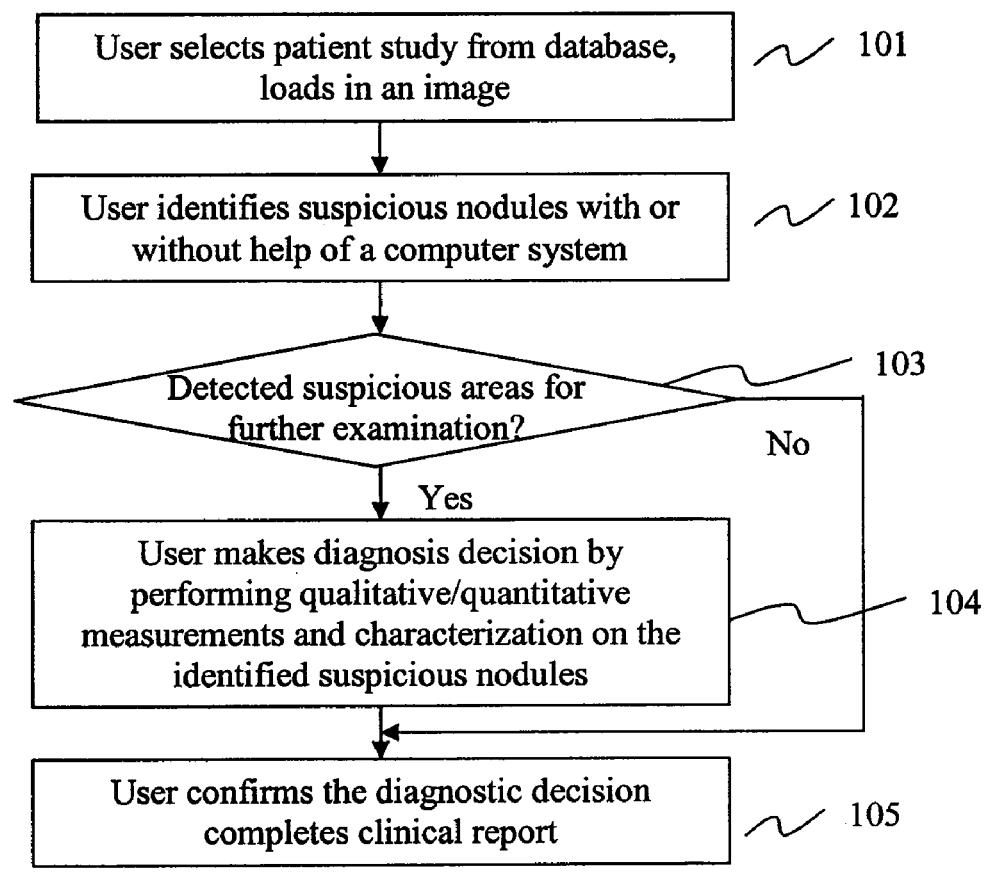
FIG. 1(a) illustrates an exemplary clinical workflow for examining a radiographic image.

The processing described below may be performed by a properly programmed general-purpose computer alone or in connection with a special purpose computer. Such processing may be performed by a single platform or by a distributed processing platform. In addition, such processing and functionality can be implemented in the form of special purpose hardware or in the form of software or firmware being run by a general-purpose or network processor. Data handled in such processing or created as a result of such processing can be stored in any memory as is conventional in the art. By way of example, such data may be stored in a temporary memory, such as in the RAM of a given computer system or subsystem. In addition, or in the alternative, such data may be stored in longer-term storage devices, for example, magnetic disks, rewritable optical disks, and so on. For purposes of the disclosure herein, computer-readable media may comprise any form of data storage mechanism, including such existing memory technologies as well as hardware or circuit representations of such structures and of such data.

This invention discloses systems and methods that facilitate integrated platform(s) capable of facilitating diagnosis information extraction and analysis to support diagnostic decision making. In some embodiments, the disclosed invention is applied to digital/digitized radiographic image softcopy reading. Assistant functions may be provided in real time interactive fashion so that the assistant functions may be embedded in an optimal workflow. Functionalities facilitating digital/digitized radiographic image softcopy reading may include, for instance, image displaying, disease-specific enhanced image viewing, annotating, automatic nodule detection, real-time interactive nodule detection and segmentation, automatic structural clinical reporting, etc. By encapsulating diagnostic information of high dimension into multiple assistant tools, and organizing such assistant tools to form multiple diagnosis scenario platforms, the disclosed system and method assist a user in reaching a medical diagnosis decision in a manner consistent with clinical practice workflow. The disclosed system may be used for different purposes, including medical and non-medical. For example, it may be used as a marking tool in an educational system in full or partial functions.

In some embodiments, the disclosed invention facilitates a plurality of features, such as one or more platform(s) and/or mechanism to support softcopy reading of digital/digitized radiographic images in a manner consistent with existing clinical workflow, an open system architecture having a diagnostic-information-oriented encapsulated hierarchy, assistance tools that allow a user to interact with the system in real time, and new algorithms enabling assistance to be rendered for medical diagnosis.

In some embodiments, the system and method may be utilized in a manner consistent with existing physicians' diagnosis workflow, including reading images to identify suspicious lesions/nodules, decision making based on qualitative and/or quantitative examination and characterization, and/or clinical report generation. For example, the disclosed system may support different groups of functionalities via distinct platforms such as an Image Reading Platform, a Matrix of Diagnosis Decision Platform, and a Clinical Reporting Platform. Intelligent assistant toolkits may be provided in a real-time and interactive manner to facilitate physicians in manipulating the system components in a manner consistent with their own working styles.

In some embodiments, the system and method may have an open architecture with a diagnostic-information-oriented encapsulated hierarchy, in which diagnostic information of different types at different levels may be encapsulated in appropriate toolkits. Such hierarchical and encapsulated architecture may make system expansion feasible to, for example, handle emerging information as modern technologies develop rapidly. Encapsulated packages containing both data and tools may be delivered across different diagnostic workstations, either locally or remotely, so that users at different locations may deploy such tools to access data encapsulated in a delivered package.

In some embodiments, the system and method may provide automatic analysis means in a real-time interactive manner to aid users in softcopy examination of patient images. Some of the automatic analysis methods performed in a real-time interactive manner may include interactive object segmentation and interactive object detection. The system may be open or transparent to users and may allow objective quantitative analysis performed by the system to be integrated with a physician's specific knowledge and/or experience to, for instance, improve performance in reaching diagnostic decisions.

In some embodiments, the system and method may be deployed with a plurality of techniques that enable emulation of a spider in catching food so that target lesions may be adaptively captured and automatically segmented to aid physicians' qualitative and quantitative analysis.

In some embodiments, the system and method may provide other functions, including intelligent automatic nodule detection on the entire image, intelligent real-time interactive nodule detection, real-time interactive intelligent nodule segmentation and quantification, real-time manual nodule segmentation and measurement, nodule-specific image enhancement, automatic clinical report generation. Those exemplary functions may be applied to lung nodules. Each of the exemplary functions is described below.

In some embodiments, the intelligent automatic nodule detection on the entire image may be activated or triggered through a single mouse click on a button or from a menu. Upon being activated, the functional component corresponding to the function may automatically identify a target region such as a lung region and scan the region for each suspicious area that possibly contains a lesion. Such automatic detection may be carried out concurrently with a user's (e.g., a physician's) manual and/or interactive examination on the same studies with additional tools that may reside on a same workstation or a different workstation located remotely.

In some embodiments, a user may interact with the automatic nodule detection component so that wherever the user points at a specific region in an image, the system may provide, in real-time, its automatic examination decision as to whether the specific region indicated corresponds to a nodule or not. In addition, the system may also provide a confidence measure with its decision indicating a level of confidence with respect to the decision.

In some embodiments, a user may not be required to trace the boundary of a nodule in order to derive a segmentation of an underlying nodule. Instead, the user may draw a rectangle around the nodule and the system may then automatically extract the boundary of the nodule. The system may also automatically compute clinically meaningful features with respect to such segmented nodule. Examples of such meaningful features include measurements characterizing the segmented nodule that may be important or helpful in assisting a user to make a diagnostic decision. Such measurements may include the size, shape, smoothness of the nodule's boundary and the intensity distribution within the nodule. In some embodiments, a user may be provided with an option to manually segment a nodule and make measurements. In other embodiments, a user may perform some manual measurement and the system may automatically compute other features accordingly.

In some embodiments, the nodule-specific enhancement may be a real-time interactive assistant tool. In some embodiments, the nodule-specific enhancement may be provided for lesion enhancement. The nodule specific enhancement may be applied on the fly to an area to where a user may have moved a cursor. Such performed disease-specific enhancement may provide a nodule-specific enhanced view of the suspicious region and the enhanced view may be magnified and displayed in a window that is adjustable both in size and in shape.

In some embodiments, the disclosed system and method may allow a user to verify each of identified suspicious nodules that are to be reported. A detected nodule that is confirmed to be reported may be automatically exported, along with its quantitative measurements, to a clinical report, which may be read, printed, saved, and reloaded whenever needed.

In some embodiments, the disclosed system and method may automatically make appropriate adjustment to its operational parameters to be able to properly operate in a dynamic environment. For example, depending on a display environment, the operational parameters used in displaying a graphical user interface may be automatically adjusted based on, for instance, the type of monitor used. In another example, font size may be automatically adjusted according to the resolution of the display monitor used. Texts and graphic objects display in the system may also be automatically adjusted, e.g., shadow may be automatically added to provide a better contrast in a displayed image that has a relatively high or a relatively low intensity.

FIG. 1(a) is a flowchart of an exemplary process for softcopy reading. A user may read, at 101, a digital/digitized radiograph image, and identify, at 102, suspicious regions with or without the assistance of a computer system. When further examination of a detected suspicious area is considered necessary, at 103, a detailed examination or analysis, either qualitative or quantitative, may be carried out, at 104, to characterize the suspicious region. Such characterization may provide evidence for diagnosis. Based on such evidence, a diagnosis decision may be made and a clinical report may be generated at 105.

Figure 1B:
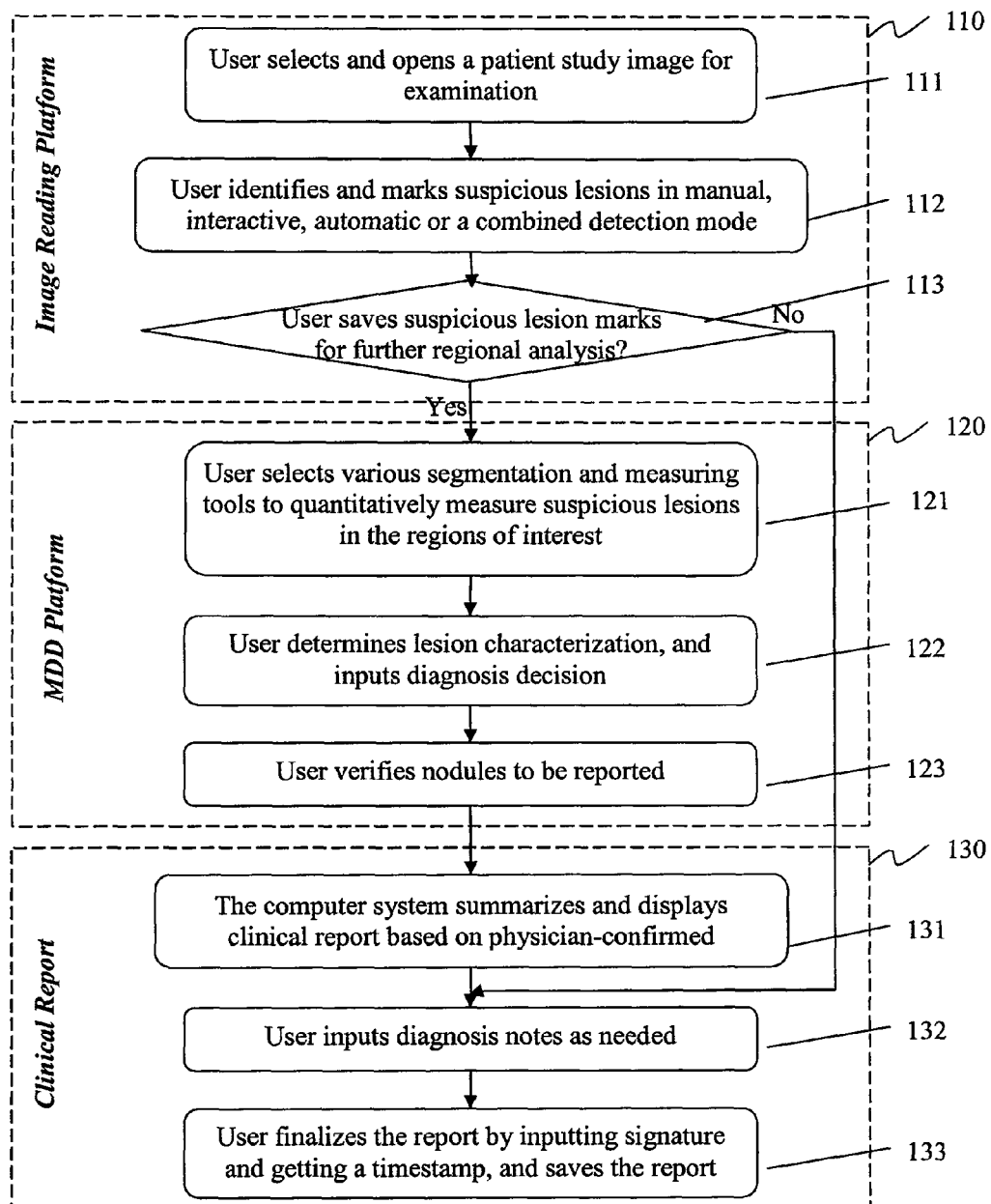
FIG. 1(b) depicts an exemplary encapsulated structure of the disclosed digital/digitized radiograph softcopy reading system.

In some embodiments, computer assistant toolkits may be grouped and encapsulated in multiple packages so that such tools may be utilized in a manner consistent with an existing clinical workflow. In addition, computer assistant tools may be provided in a real-time and interactive fashion so that they may be embedded in an optimized workflow. An exemplary embodiment of the encapsulation architecture with corresponding functions is illustrated in FIG. 1(b). In this exemplary embodiment, three encapsulated assistant packages may be grouped, including an Image Reading Platform 110 enabling a user to identify suspicious nodules, a Matrix of Diagnosis Decision (MDD) Platform 120 providing a platform where a user may reach a diagnosis decision based on evidence derived from qualitative/quantitative measurements/characterization, and a Clinical Reporting Platform 130 enabling generation of summary of information associated with a diagnosis and saving of a diagnostic record. Each of the exemplary platforms is described in detail below.

Image Reading Platform

Figure 2A:
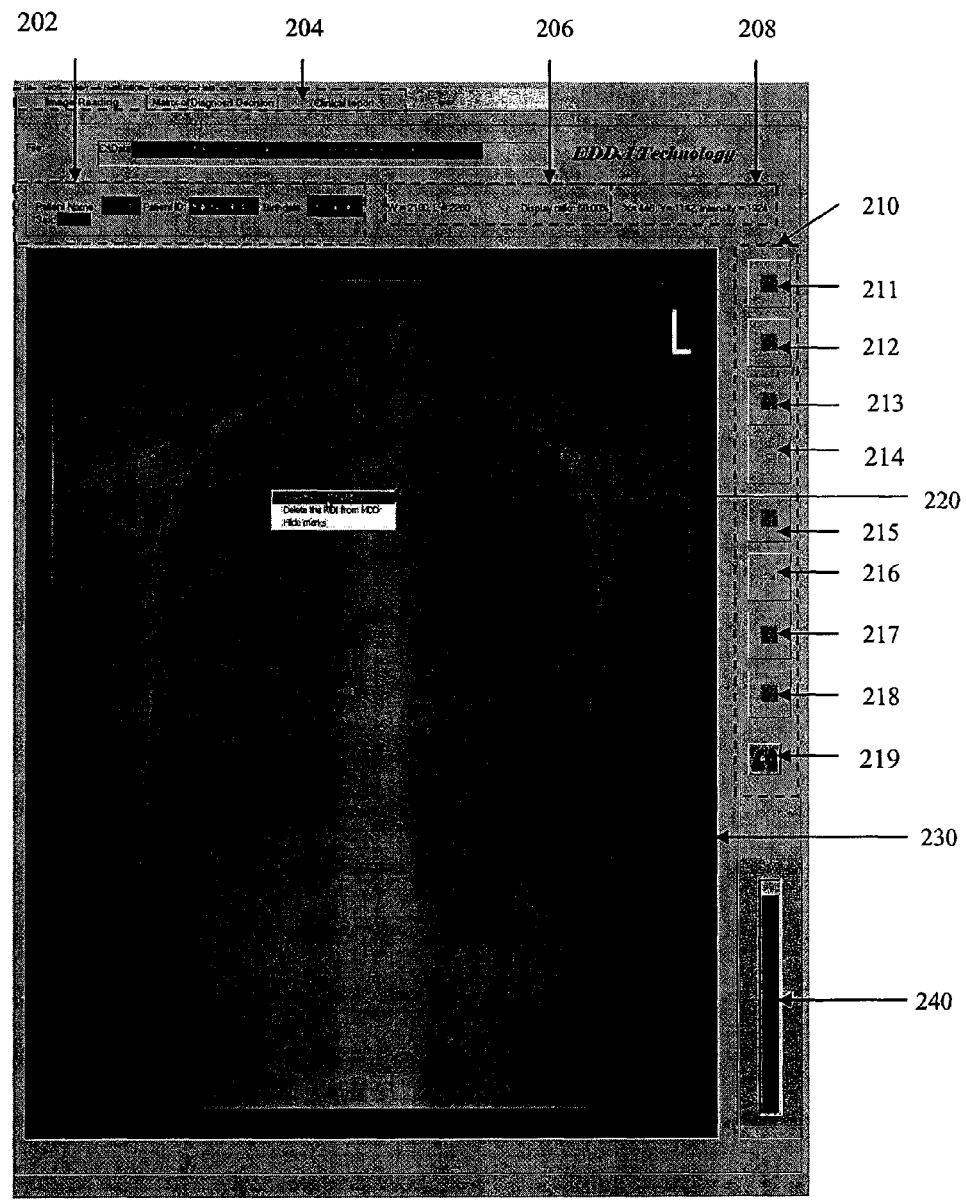
FIG. 2(a) shows an exemplary GUI displayed on a portrait monitor.
Figure 2B:
FIG. 2(b) shows an enlarged picture of a tab controller.
Figure 2C:
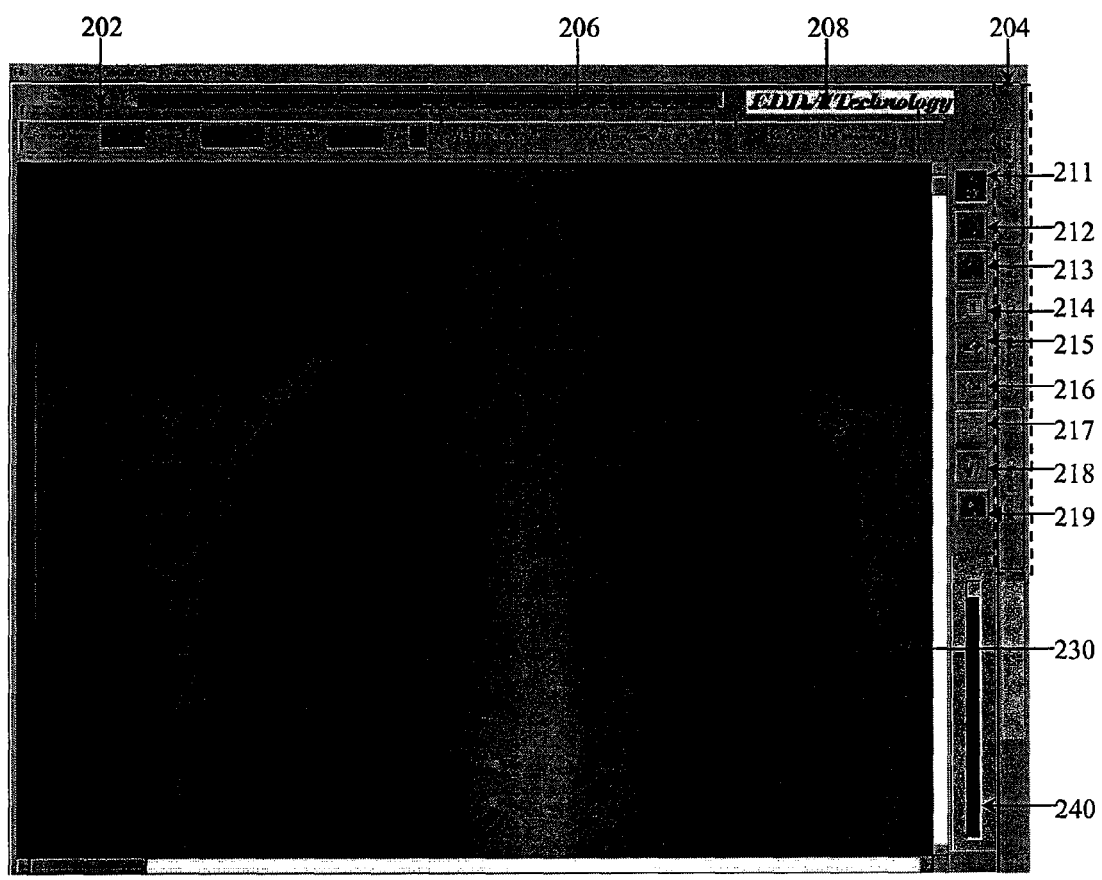
FIG. 2(c) shows an exemplary GUI displayed on a normal monitor.

In operation, a user may trigger the Image Reading platform 110 in order to start softcopy reading. A user may activate any assistant tool encapsulated in this platform or a combination thereof to read an image associated with a patient and/or to identify a suspicious region within the image. An exemplary display of the Image Reading Platform displayed on a portrait monitor is shown in FIG. 2(a). The exemplary Image Reading Platform comprises a plurality of fields. Examples of included fields may be, a patient information field 202, a tab controller 204 that is accessible in all platforms so that a user may switch back and forth among different diagnostic stages, a display/viewing parameter field 206, a cursor position and pixel intensity field 208, a toolbar for interactive assistant tools 210, which may further comprise a patient file selection and open functional icon 211, a window level setting adjustment functional icon 212, a functional icon 213 to control the display of a user's mark, a functional icon 214 for a batch mode automatic nodule detection on multiple images, an undo button 215, a redo button 216, a functional icon for automatic nodule detection on a current image 217, a functional icon for interactive nodule detection on a current image 218, a nodule-specific image enhancement tool icon 219, a pop-up menu having choices of functions and display settings 220, a display window 230 for displaying an image during, e.g., nodule detection, and an interactive detection confidence bar field 240, which may pop up when the interactive detection icon 218 is activated. An Image Reading Platform may be displayed according to automatically adjustable display parameters. For example, FIG. 2(c) illustrates a display of an Image Reading Platform displayed on a regular monitor. An enlarged view of the tab controller 204 for switching among different diagnosis stages is illustrated in FIG. 2(b).

Based on an Image Reading platform, a user may load a patient image and display such loaded image in the display window 230. Once a patient image is loaded and displayed, a user may identify a suspicious nodule region in different operational modes such as in a manual detection mode, in an automatic detection mode, in an interactive detection mode, or in a combined mode.

Figure 3A:
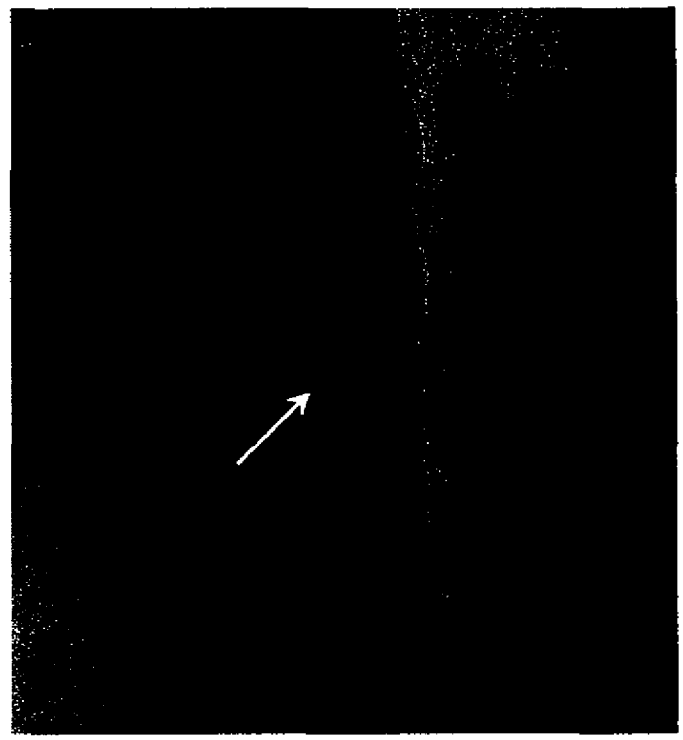
FIG. 3(a) shows an original image with an arrow pointing at a nodule.
Figure 3B:
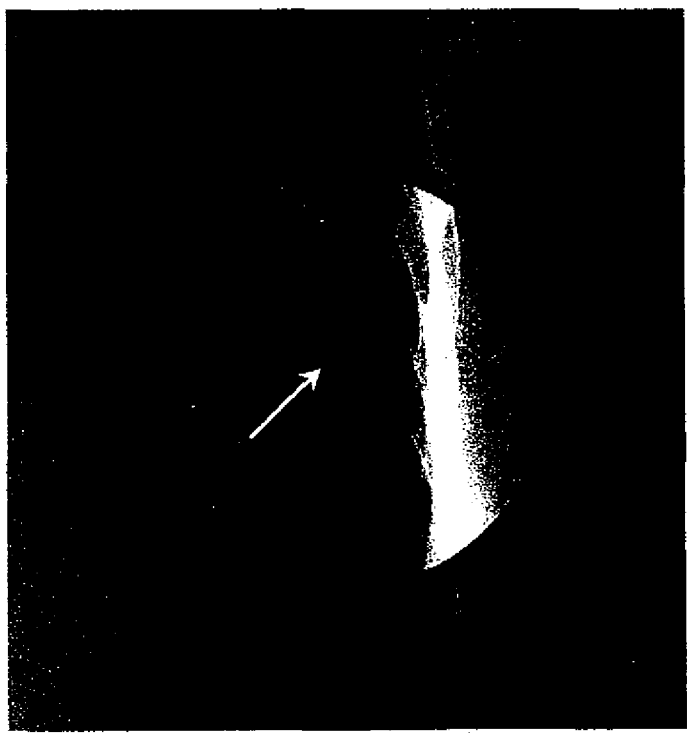
FIG. 3(b) shows an image with nodule-specific image enhancement.

In a manual detection mode, a user may identify nodules with or without the help of assistant tools provided in the Image Reading platform. For example, a user may specify a suspicious region by manually pointing at the region via, e.g., a mouse click on a displayed image. When a nodule candidate is identified, a user may add the detected nodule to a Diagnosis Information Table described below with respect to Matrix of Diagnosis Decision (MDD) Platform. In some embodiments, a user may identify a suspicious region with the help of the system. For example, real-time interactive assistant tool Nodule-specific Image Enhancement tool 219 may be activated to first perform disease-specific image enhancement which may yield imagery within a region that has enhanced perceptual effect to help the user better understand complex structures within the enhanced region. In some embodiments, such enhancement may be applied on a region of interest (ROI) centered around a dynamic cursor position. The size of a ROI around a dynamic cursor position may be predetermined, dynamically computed based on image features, or manually adjusted. The shape of such a ROI may be different in different embodiments. For example, a ROI for enhancement may be circular shape, elliptical shape, or rectangular shape. Magnification may be applied during enhancement. In some embodiments, the degree of magnification may be continuously adjusted by, e.g., dragging the mouse with, e.g., the right button down. FIG. 3(a) shows an example of a part of a chest radiographic image where a nodule is indicated by an arrow. FIG. 3(b) shows the same image with an enhanced region where the enhancement is achieved using an nodule-specific image enhancement tool. In this example, the shape of ROI used by the nodule-specific image enhancement tool is a circle.

In some embodiments, automatic nodule detection may be facilitated. An example of a nodule may be a pulmonary nodule. Different methods to activate automatic nodule detection may be implemented. For example, such detection may be triggered via a single mouse click on corresponding tool icon 214 or through a menu selection. Once the detection is activated, the system may automatically scan the patient image to detect for nodules/lesions. Details of nodule detection are discussed below. If a suspicious nodule structure is identified, information associated with the suspicious nodule structure may be stored for, e.g., additional examination, which may be performed manually by a user, automatically by a computer system, or interactively through human-machine interaction.

An identified suspicious nodule may be presented or displayed via different means. In some embodiments, a mark may be displayed nearby the detected suspicious structure pointing at a suspicious nodule area. In some embodiments, a user may be requested to determine whether the indicated structure corresponds to a likely nodule, whether the detected suspicious structure needs further examination, or both. In some embodiments, when either the suspicious nodule is likely to be an actual nodule or the detected nodule may require further examination, information related to the detected nodule candidate may be automatically added to a Diagnosis Information Table. Details related to the Diagnosis Information Table are discussed below in describing Matrix of Diagnosis Decision Platform.

Figure 3C:
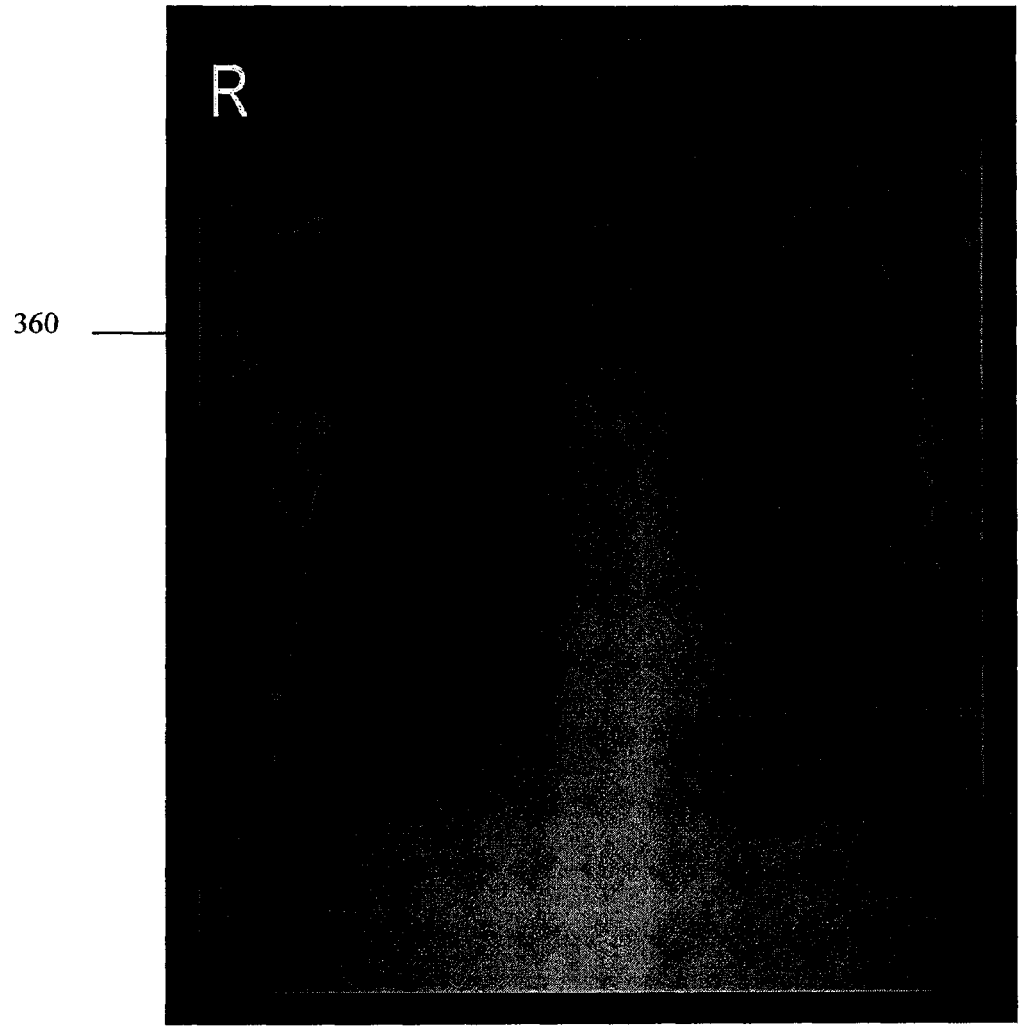
FIG. 3(c) is an example of presenting automatic lung nodule detection results by highlighting the suspicious regions.
Figure 3D:
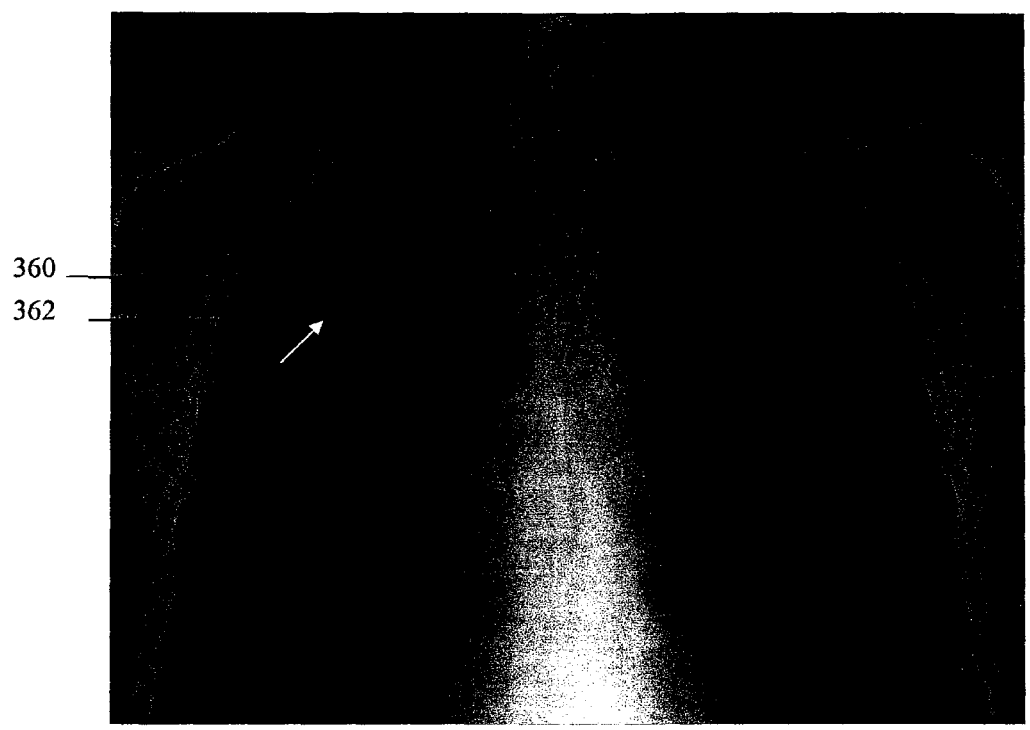
FIG. 3(d) is an example of applying nodule-specific image enhancement to an automatically detected suspicious nodule region highlighted by the computer.

In some embodiments, a region containing a detected nodule/lesion may be highlighted to provide an enhanced viewing effect. Highlighting the suspicious ROI may serve to catch a user's attention. The highlighting may be achieved via different schemes that differentiate the intensity levels of the suspicious region and the rest of the image. For example, it may be carried out by increasing the intensity contrast displayed within a suspicious region while keeping the intensity contrast of the rest of the image the same. Alternatively, this may be achieved by decreasing the intensity contrast displayed in the rest of the image while keeping the intensity contrast of a suspicious region the same. As another alternative, this may also be achieved by simultaneously increasing the display intensity contrast of a suspicious region and decreasing the display intensity contrast in rest of the image. The highlighting effect may also be achieved by making the intensity level of the suspicious region lower than that of the rest of the image. In addition, given that the leveling of image display in a window may be optimized by a user, one may also choose to keep the current optimized display settings for a suspicious region and dim out the rest of the image so that the suspicious region may visually seem to be highlighted. FIG. 3(c) shows an example display of a nodule that is automatically identified. In this example, an automatically identified suspicious region 360 is "highlighted" to catch a user's attention. In some embodiments, a user may utilize a nodule-specific image enhancement tool in combination with a marked view mode or a region-highlighted view mode to locate suspicious structures. FIG. 3(d) illustrates a display in which nodule-specific image enhancement is applied to a detected suspicious region highlighted.

In some embodiments, more than one detected nodule may be grouped in a single highlighted region covering them all. This may be adopted when different nodules are close by so that a single highlighted region with highlighted view may visually avoid a cluttered display. When window level settings are changed (e.g., by a user), a display of a suspicious region and the rest of the underlying image may be adjusted accordingly, while the contrast between the suspicious region and the rest of the image may be kept the same to maintain the "highlighting" effect. In some implementations, a user may be allowed to freely switch between a normal image viewing mode and a view in which a nodule is indicated. The scheme of highlighting a region to caution a viewer may also be applied in other scenarios other than detected nodule candidates. For example, it may be applied to other types of diseases or information of different modalities.

In some embodiments, automatic nodule detection may be performed in a batch mode for multiple images pre-selected. For example, a user may select multiple patient studies and submit a batch job so that detection may be performed on all selected images in a batch to automatically identify nodules contained in such images.

In some embodiments, a user may identify nodules in an interactive mode. In some embodiments, this interactive nodule detection mode may be activated via a single mouse click on, for example, a corresponding tool icon 216. In this mode, a user may point at a region in an image and then an automatic nodule detection module may operate in real-time to yield an output indicating whether there is a nodule nearby that particular location/region or not. Such an output may be provided with a confidence measure, which may be displayed in different visually informative forms such as a bar or a pie, 220. The confidence measure may provide a user a reference with respect to a diagnosis decision as to whether the current structure near the indicated region corresponds to a nodule or not. A suspicious region may be saved for further examinations. In some embodiments, nodule detection may also be performed in an operational mode that is a combination of the above three described detection modes. Other assisted tools available from the Image Reading Platform may also be activated in connection with nodule detection.

Some operations that can be activated may be time consuming. In some embodiments, to meet speed requirements in clinical practice and/or to improve clinical throughput, the operation(s) performed under any of the platforms may be optimized. For example, processes may be performed simultaneously in front and back ends. In some arrangements, time consuming processes are performed in the backend and real-time functions are performed in the frontend. Time consuming processes may include, for instance, some information preparation functions or benchmark automatic nodule detection.

Figure 4A:
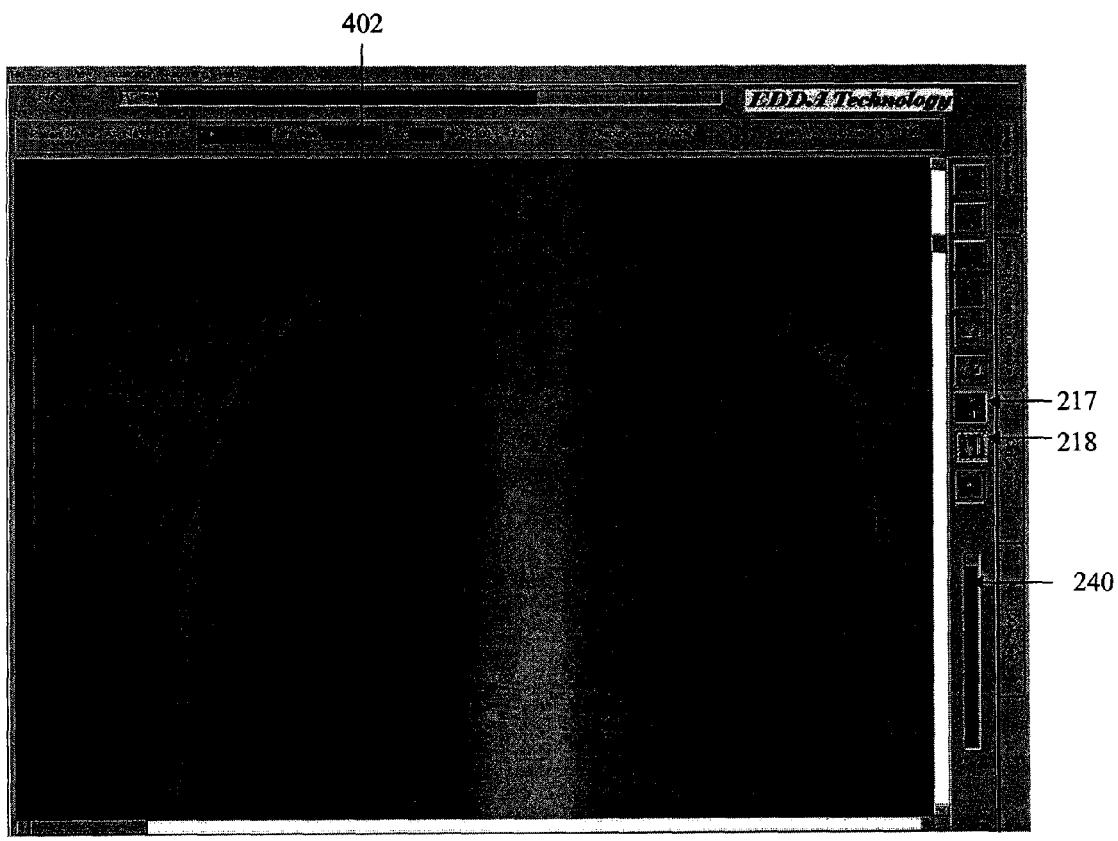
FIG. 4(a) is an exemplary GUI allowing concurrent diagnosis operations.
Figure 4B:
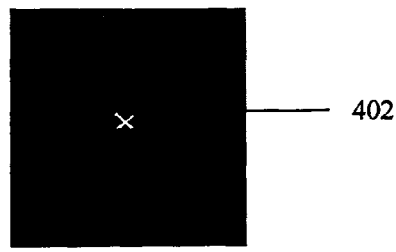
FIG. 4(b) shows an example of a ROI with a mark indicating a nodule.

In some embodiments, the operational status of a process running in the backend may be visually indicated through, for example, a display of a pie or others. Such a display may be at the same location as the original tool icon. Putting the tool icon and corresponding processing status at the same location may make it easier for a user to remember which task is currently in progress. FIG. 2(c) illustrates an exemplary interface showing that backend and frontend concurrent processes are in execution. FIG. 2(c) shows that when a patient image is loaded, a function runs in the backend that is extracting certain information that may be helpful for a physician's interactive analysis of the image while a processing status is displayed at or near an "Open" icon 211. Alternatively, a user may concurrently perform diagnosis using other assistant tools based on existing information and before the whole information extraction completes. FIG. 4(a) illustrates another example where interactive detection is running in the frontend and a benchmark automatic nodule detection process is running in the backend simultaneously. In this example, a processing status associated with automatic nodule detection icon 217 is displayed indicating that the automatic nodule detection is running in the backend. An interactive nodule detection icon 218 indicates that interactive nodule detection is concurrently in progress. A confidence bar 240 with a range, for instance, from 0.0 to 1.0 may indicate a likelihood with regard to the presence of a nodule within a current object of interest 402. FIG. 4(b) shows an enlarged view of block 402 in FIG. 4(a), which, for example, indicates that a current object of interest being examined by the Interactive Detection may correspond to an actual nodule.

In some embodiments, a time consuming process may be canceled at anytime by a user. In some embodiments, a progressive indicator may serve as a cancel button. A user may click on a progress indicator to terminate an ongoing background process.

In some embodiments, different functions may be automatically configured based on data flow dependency. For example, a function that takes the output of one or more other functions as its input may be automatically activated after those other functions generate their output. As one example, when an information preparation function is still in progress, an automatic nodule detection function that carries out its process on a pre-processed image is automatically blocked at the frontend until the information preparation function running in the backend completes its operation(s).

Matrix of Diagnosis Decision (MDD) Platform

In some embodiments, the Matrix of Diagnosis Decision (MDD) Platform facilitates various functions related to diagnosis related features. For example, it may provide a platform where comprehensive diagnosis-related information may be presented, qualitative and quantitative analysis may be activated, and/or diagnosis decisions with respect to individual suspicious nodule(s) identified under the Image Reading Platform may be made. The MDD Platform may be encapsulated with various types of information, which may include non-visual information and/or visual information. Visual information may include patient information, medication history, lab report(s), image data information, and/or genotype information. Visual information may include image data and/or pathologic images. The MDD platform may also include real-time interactive toolkits encapsulated with different diagnostic information.

In some embodiments, non-visual information may be disease-specific and/or patient-specific and such information may be used by a user in diagnostic decision making. For example, patient specific information may be used to make a qualitative assessment as to a level of risk for the patient to have a specific type of disease. Some prior knowledge related to a patient, such as key evidence indicating that the patient is at high risk for a specified disease and/or that some important parameters may be out of normal ranges, may be highlighted when displayed to provide a warning signal to users. In addition to non-visual information, image related information may be analyzed to derive information relevant to diagnostic decision making. Such analysis may be qualitative or quantitative and the analyzed result may be visualized and further statistically analyzed. In some embodiments, such diagnostic related information, either visual or non-visual, may be encapsulated in different interactive real-time toolkits with functions that a user may invoke to assist diagnostic operations.

Figure 5A:
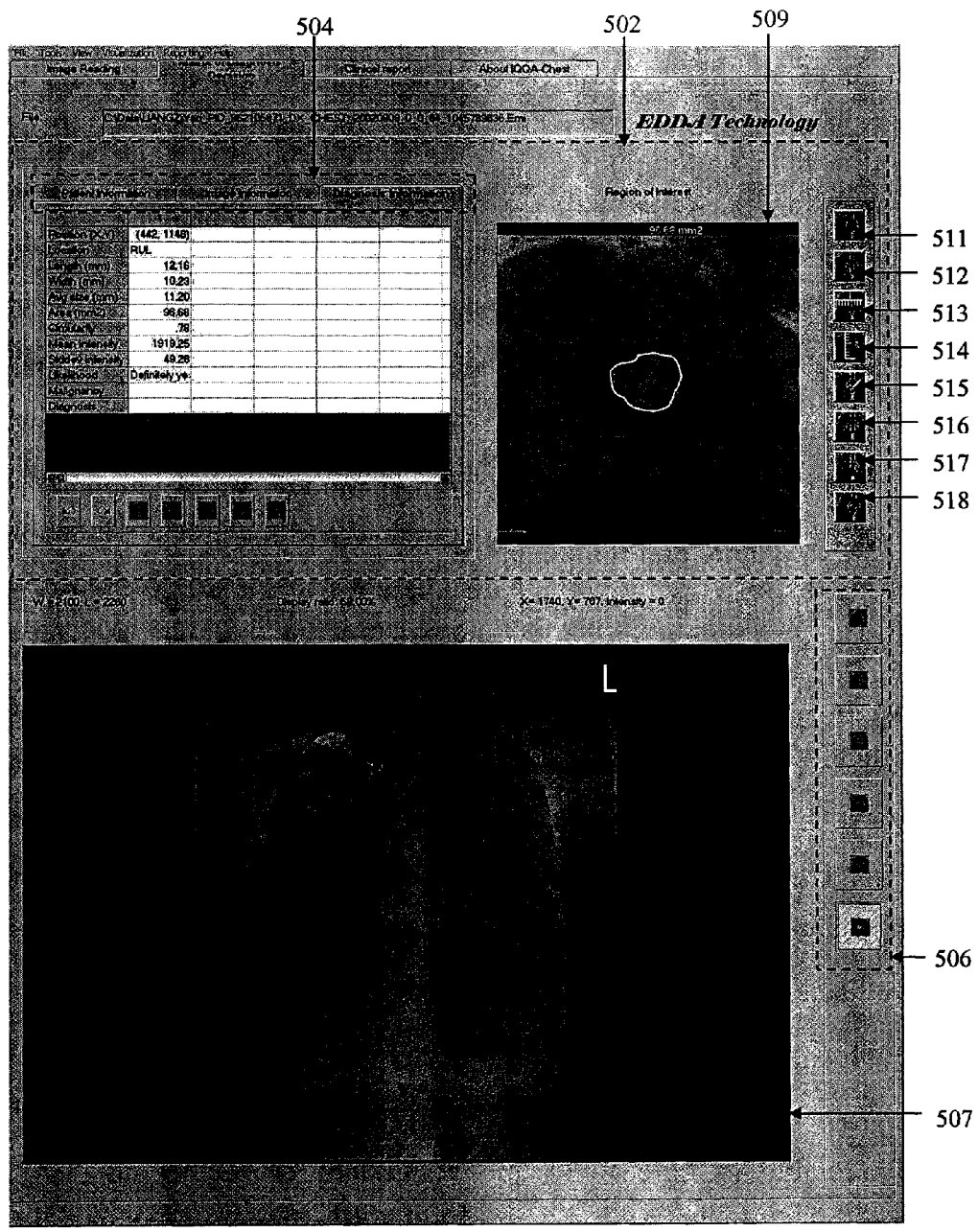
FIG. 5(a) shows an exemplary Matrix of Diagnosis Decision (MDD) Platform displayed on a portrait monitor.
Figure 5B:
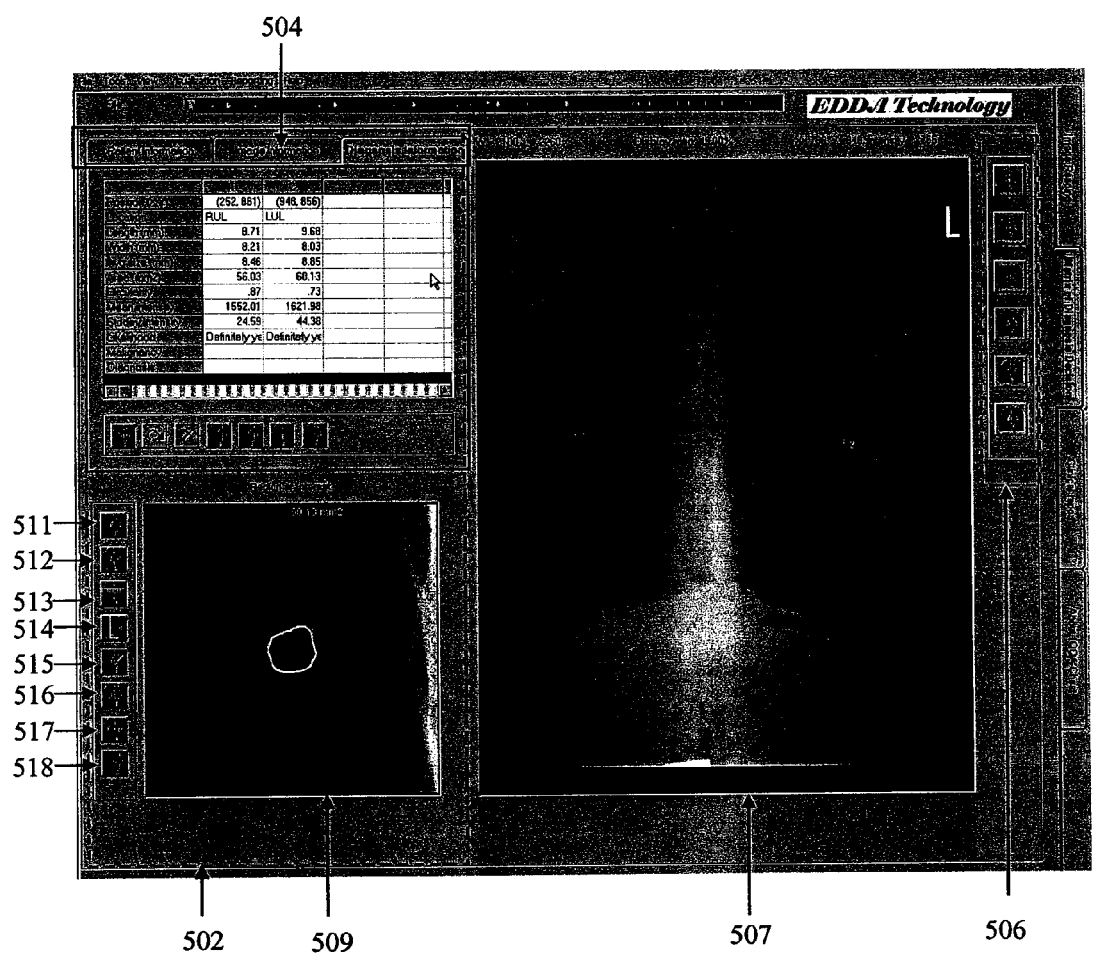
FIG. 5(b) shows an exemplary Matrix of Diagnosis Decision (MDD) Platform displayed on a normal monitor.

FIG. 5(a) shows an exemplary MDD Platform displayed on a portrait monitor. FIG. 5(b) shows an exemplary MDD platform displayed on a conventional monitor. The display of the MDD platform may be automatically adjusted according to the type of monitor used in practice. In the illustrated exemplary MDD platform, the MDD Platform may comprise a Diagnosis relevant Information Card 502, and a patient image display field 507 with associated assistant functions 506. The Diagnosis Relevant Information Card 502 may provide visual and non-visual information that may be used to assist diagnosis decision making. Such information may be displayed or invoked in a working area through various encapsulated assistant tools. Different types of visual and non-visual information may be selected using the tab controller 504. Patient related information may be viewed and manipulated using various tools made available through the encapsulated assistant tools in 506. In the illustrated exemplary MDD platform, when Diagnosis Information is selected, the corresponding encapsulated assistant tools are activated, which comprises a display area 509 in which a region of interest containing a detected nodule is displayed, and associated interactive assistant functions 511 to 518.

The MDD Platform may provide various diagnosis assistant tools. For example, it may provide tools 506 for displaying and visualizing a patient image. Such visual display of patient image data may provide a reference based on which a diagnostic decision is made. Based on such a displayed image, a user may retrieve information associated with the displayed image. For example, information retrieved may indicate in which lung lobe a suspicious nodule is located, whether a suspicious nodule is connected to other anatomic structures, such as vessels or diaphragm, whether there are other abnormalities that may be related to a detected nodule, etc. Such information may be important to a user in reaching a diagnosis. In some embodiments, similar assistant tools as those described with respect to the Image Reading Platform may be encapsulated with a patient image. For example, it may include a Nodule-specific Image Enhancement tool, a tool for nodule candidate mark display or hide, a tool for window leveling, or a tool for image zooming (e.g., zoom in or zoom out, etc.).

Figure 6:
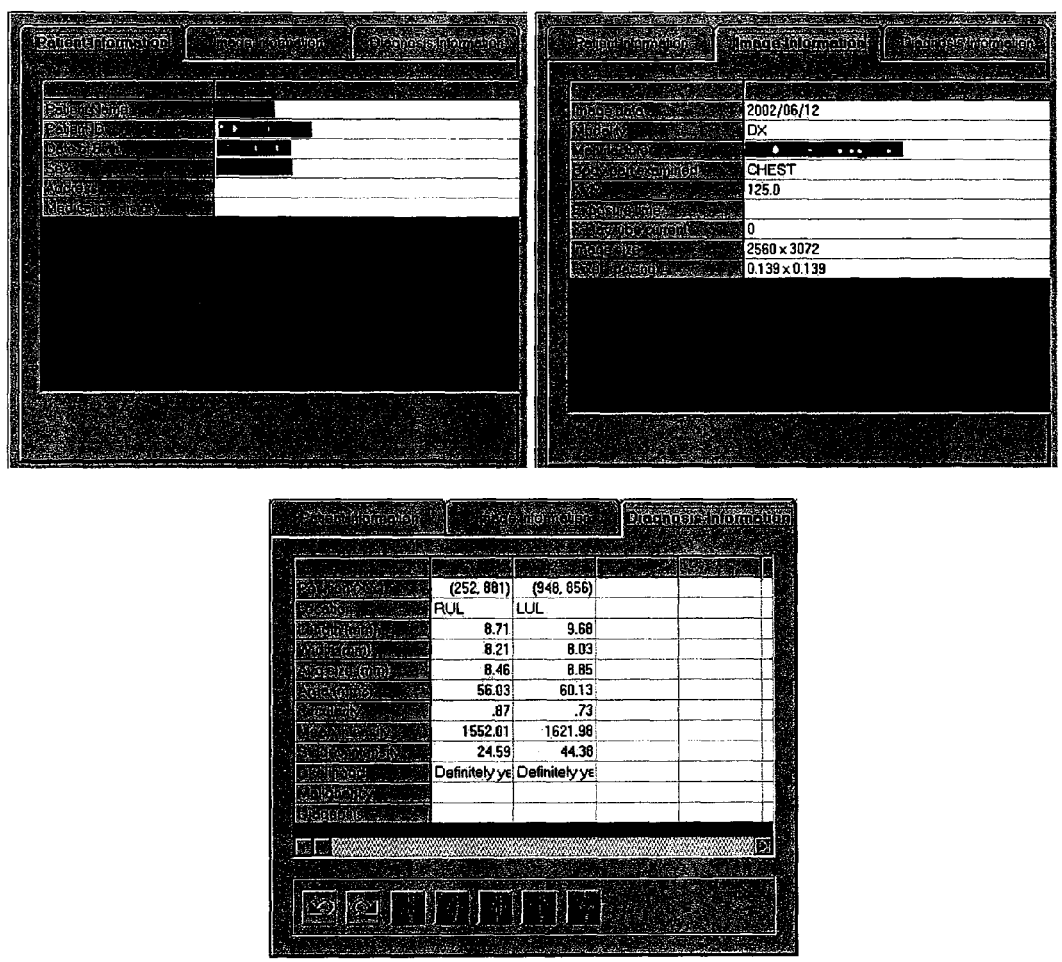
FIG. 6 shows an exemplary Diagnosis Relevant Information Card.

The Diagnosis Relevant Information Card 502 in the MDD Platform may be encapsulated with different assistant tools. The Diagnosis Relevant Information Card 502 may provide visual and non-visual information, which may be encapsulated with different manipulation tools such as the means to generate qualitative and quantitative measurements on such information. An exemplary GUI for the Diagnosis Relevant Information Card 502 is shown in FIG. 6. In this example, the Diagnosis Relevant Information Card 502 comprises a plurality of information groups, including, for instance, a patient information table, an image information table, and a diagnosis information table. Contents in these tables may be dynamically updated or extended.

In some embodiments, the Diagnosis Relevant Information Card 502 may be configured to further possess different features. For example, the Diagnosis Relevant Information Card 502 may be an encapsulation in a high-dimensional space. It may also be configured so that it may include as many categories of information as needed and with as many levels of diagnosis related information as needed. For example, the Diagnosis Relevant Information Card 502 may be extended to have an additional category of genotype information represented using, for instance, a Genotype Information Table. In addition, each table may also be extended. For example, the Patient Information Table may be extended to include a new sub table containing information related to Previous Medication History.

In some embodiments, an information table in the Diagnosis Relevant Information Card 502 may be implemented as an encapsulation with both diagnostic related information and functions that can be used to manipulate the corresponding information. Such encapsulation may make diagnosis based on relevant information more effective. For example, if a Patient Information Table is selected, other types of information related to the selected patient may be automatically retrieved such as certain statistics associated a particular disease that the patient is suspected to have. An encapsulated tool may then use such retrieved information to, for example, further identify key evidence indicating e.g., that the patient may be at high risk for a disease and highlight those key parameters that are out of normal ranges to catch attention of medical personnel. In another example, a user may utilize an encapsulated tool to interactively adjust a reference range of a particular parameter. Such operations may be performed within the encapsulated Patient Information Table.

Figure 7:
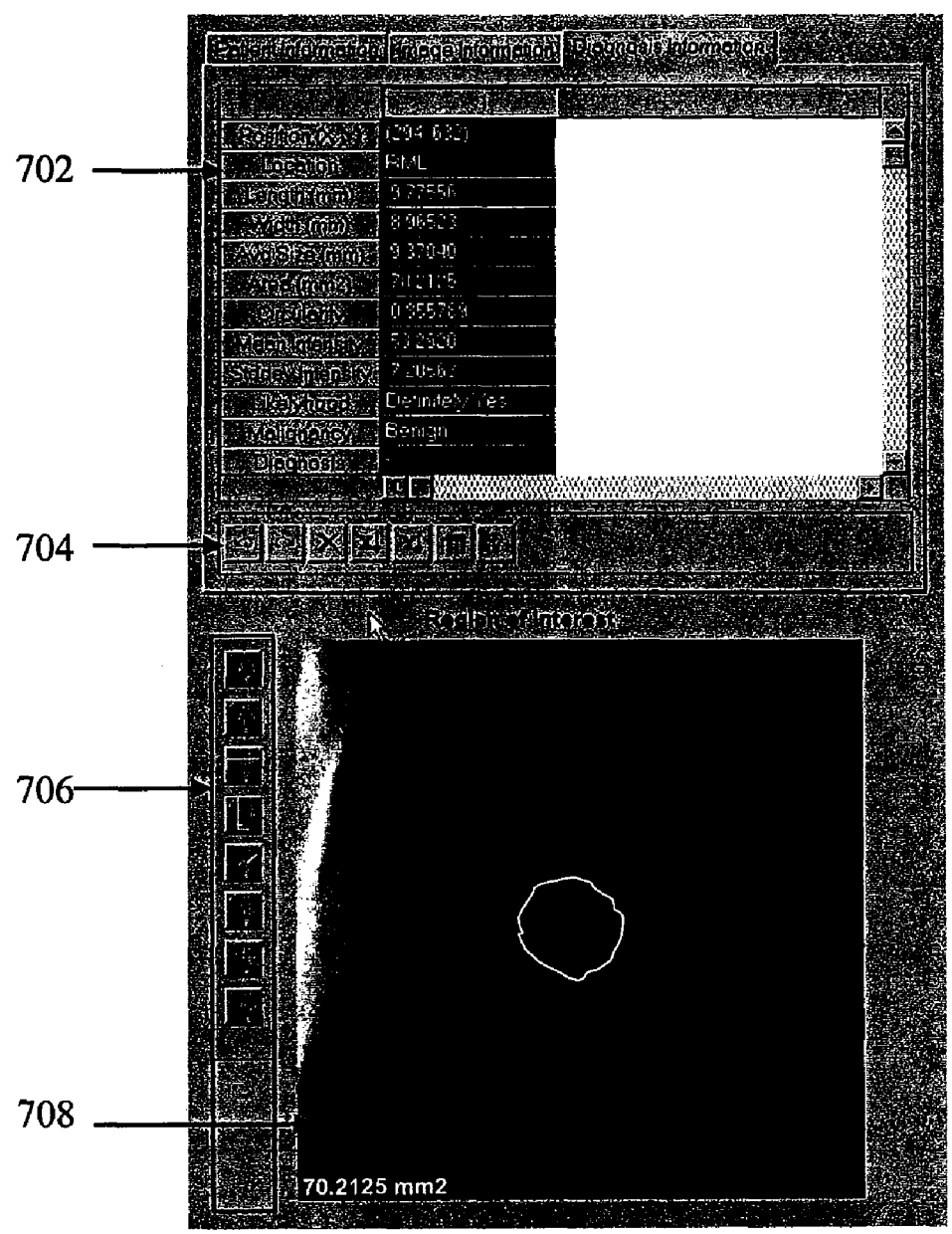
FIG. 7 shows an example of an encapsulated Diagnostic Information Table.

In some embodiments, whenever a table is selected, its corresponding encapsulated assisted tools may be made available. For example, when a diagnostic information table (see FIG. 6) is selected, activation buttons corresponding to tools encapsulated with the information in the selected table (e.g., tools that assist qualitative and quantitative measuring of suspicious nodules in an image) may be displayed, for example, underneath the selected table itself. FIG. 7 illustrates such an example, in which a diagnosis information table is selected and various activation buttons (e.g., in the form of icons) associated with encapsulated assisted tools for manipulating information in the selected table may be displayed below the table itself. In this example, the diagnostic information table 702 includes different quantitative measurements made with respect to a nodule detected and marked in a region of interest (or an area suspected to have a nodule) as displayed in 708. There are two exemplary toolbars displayed that are associated with different types of information. A toolbar 704 corresponds to tool activation icons associated with the selected diagnostic information or Diagnosis Information Table controllers and a toolbar 706 corresponds to tool activation icons for encapsulated real-time assistant tools associated with the image displayed in region 708 for diagnostic information analysis. The display area 708 may also provide an area in which manual, interactive and automatic nodule detection and qualification operations may be carried out. In some embodiments, when an alternative information diagnosis is selected, different corresponding toolkits encapsulated with the selected information may be accordingly presented.

As one may see illustrated in FIG. 5(a), a user may also select a specific nodule candidate for examination. A selected nodule may be displayed in 509. When the diagnosis information table is activated and a specific nodule candidate is selected for detailed examination, one or more assistant tools may be used to aid qualitative and quantitative analysis on the nodule. For example, such tools may include, but are not limited to, a tool 511 for window level adjustment of a subimage displayed in 509 to yield a better visual effect to support nodule segmentation, a tool for hiding or displaying a mark at the corresponding nodule position and/or hiding or displaying the extracted nodule boundary or a ruler measurement on the ROI display 509, a ruler 513 for measuring the width of a nodule displayed in 509, a ruler 514 for measuring the height of a nodule displayed in 509, a tool 515 for performing manual nodule segmentation to the nodule displayed in 509, a tool 516, for performing real-time interactive/automatic nodule segmentation to the nodule displayed in 509, and a tool 517 to display histogram information of the extracted nodule or the region of interest displayed in 509, and a tool 518 for help on use of the tools 511 to 517, etc.

The Real-time Interactive/automatic Nodule Segmentation function 516 is a nodule segmentation and assessing tool. A user may activate it to segment a suspicious nodule region by drawing a reference rectangle around the nodule on a subimage. The computer may instantaneously segment out a nodule and display the segmented result by overlaying the derived nodule boundary on the original sub-image. In some embodiments, some quantitative measures such as size, shape, smoothness of the boundary, and calcification distribution, etc., may be automatically calculated in real time and displayed in the diagnosis information table. A user may then make a diagnosis decision based on an assessment of such results. FIGS. 5(a), 5(b), and 7 illustrate a nodule boundary superimposed on an image as well as the quantitative measurements made based on the detected nodule boundary. In some embodiments, means for segmentation result correction and/or manual segmentation may also be activated to improve segmentation results yielded by the real-time interactive segmentation tools.

In some embodiments, different mechanisms may be implemented in the real-time interactive nodule segmentation and manual nodule segmentation tools to assure segmentation consistency and quality. For example, when a user draws a nodule boundary to manually segment a nodule or draw a reference box around a nodule to let the computer segment a nodule in real time (e.g., on the subimage displayed in 708), it may be automatically checked to see whether the drawn boundary or the reference box actually contains a corresponding nodule position recorded in the diagnostic information table. In some embodiments, when there is no recorded nodule within the boundary or reference box, a warning message may be provided. In other embodiments, tools may be provided to help a user locate a marked nodule position and identify the nodule boundary. For example, such a tool may include a window level adjustment 511 to enable display of a subimage for which segmentation is performed to have a better visual effect. Another example of such a tool is 512 that enables hiding or displaying a mark at a corresponding nodule position and hiding or displaying the extracted nodule boundary on the ROI image.

Figure 8:
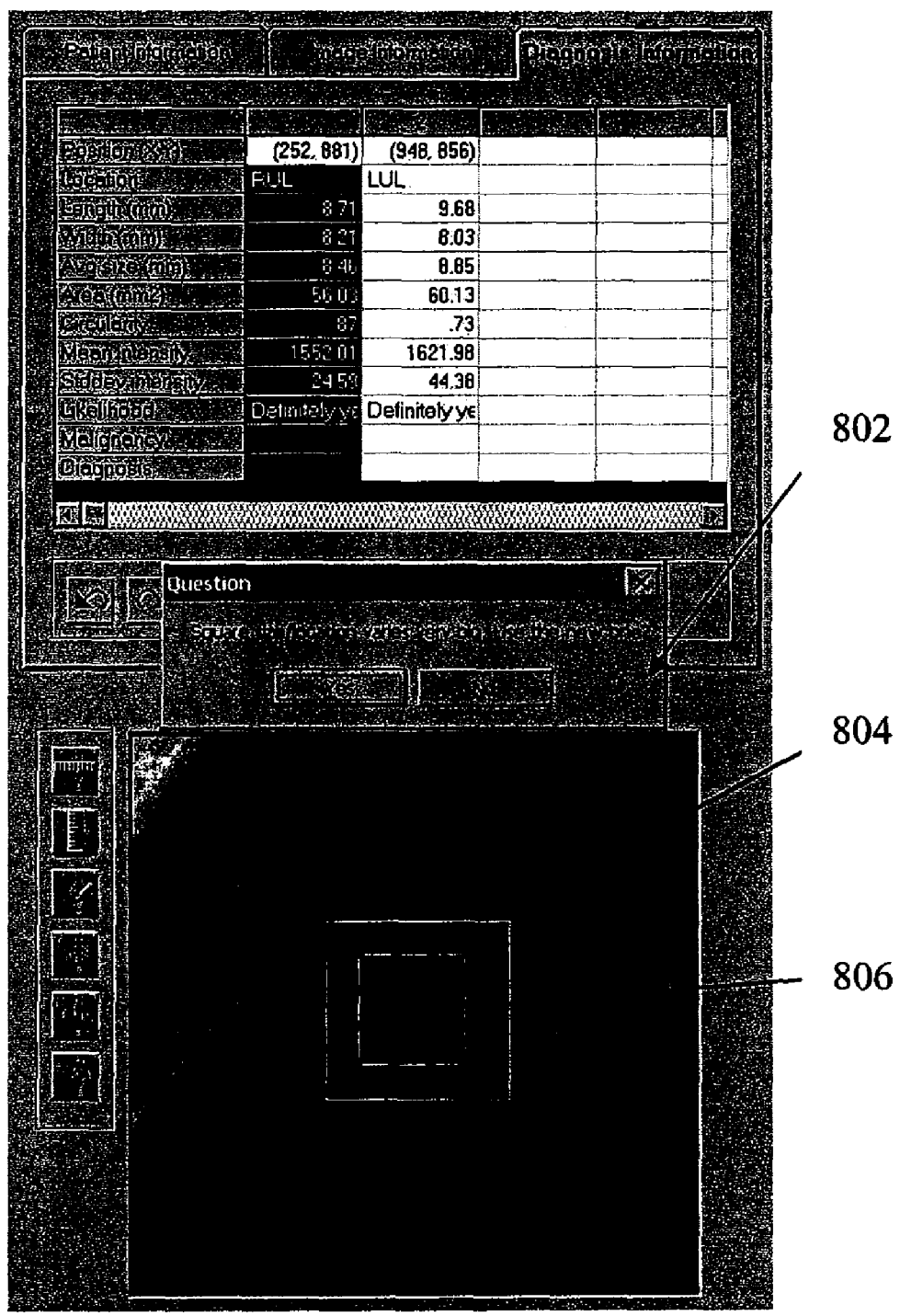
FIG. 8 illustrates an exemplary embedded consistency check during interactive nodule segmentation.

It is known that boundaries of a nodule marked by a physician at different times may vary. For example, in segmenting a nodule with a size around 5 mm, a small hand shake may cause substantial differences. The variation may be even bigger when markings are made by different physicians. In some embodiments, to reduce inconsistency among different markings made to the same nodule, a user may interact with the system to examine a segmentation result. In other embodiments, some automated examination may be imposed. In some embodiments, in using a real-time interactive/automatic nodule segmentation tool to draw a reference rectangle with respect to a nodule, the currently drawn reference box may be compared with another reference rectangle that is previously confirmed in terms of position, size, and shape. If the currently drawn reference rectangle substantially deviates from the previous one, some further action may be taken to caution a user. For example, a dialog box may pop up, warning of the discrepancy and asking a user to make a choice. Through this mechanism, a user is informed of any inconsistency. Such warning may help improve the quality of the segmentation and ultimately the diagnosis. FIG. 8 shows an example of such a consistency assurance mechanism. In this example, the dashed rectangle 806 represents a previously confirmed reference box and the solid rectangle 804 represents a currently drawn reference box. A dialog box 802 is popped up to warn a user that inconsistency between the two reference boxes has been identified after such inconsistency is automatically determined based on information associated with the two boxes. The dialog box 802 may prompt a user to make a choice between the two reference boxes. Such a choice may be made based on a user' domain-specific knowledge and/or patient-specific information.

In the example of FIGS. 5(a) and 5(b), there may be other assistant tools that may be encapsulated in different information tables of the Diagnosis Relevant Information Card. Such assistant tools may include tools for information fusion, tools for different information presentation (e.g., presentation using numbers, text and/or intuitive graphs), tools for information adaptation with respect to a user's specific knowledge and dynamic configuration, and tools for abnormality characterizing based upon images.

A user may selectively utilize the information and assistant analysis tools thereof offered by the MDD Platform. A user may also selectively use information of specific dimension(s) by examining part of the information encapsulated. In some situations, a user may check a particular aspect of the information across time line. In some situations, a user may compare a particular type of information contained in the MDD platform with statistics obtained from elsewhere (e.g., the Internet) for diagnosis purposes. Information and the analysis thereof may be accessed and performed based on needs so that throughput may be improved. Since the wealth of information is encapsulated and made easily accessible, it helps to improve the quality of diagnosis.

Clinical Reporting Platform

Figure 10:
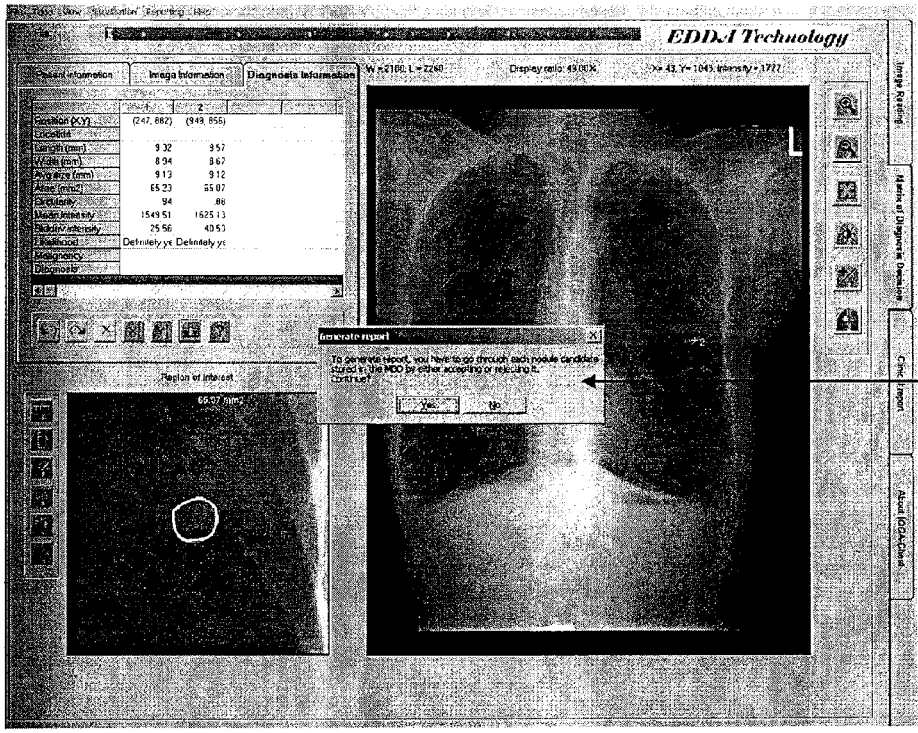
FIG. 10(a) shows an exemplary GUI with a pop-up dialog box that instructs a user to generate a report.
FIG. 10(b) shows an exemplary GUI with a pop-up dialog that requires a user to confirm the inclusion of a specific nodule in a clinical report.
FIG. 10(c) is an exemplary dialog box that instructs a user with respect to generating a report.
FIG. 10(d) is an exemplary dialog box that requires a user to confirm the inclusion of a specific nodule in a clinical report.
Figure 10:
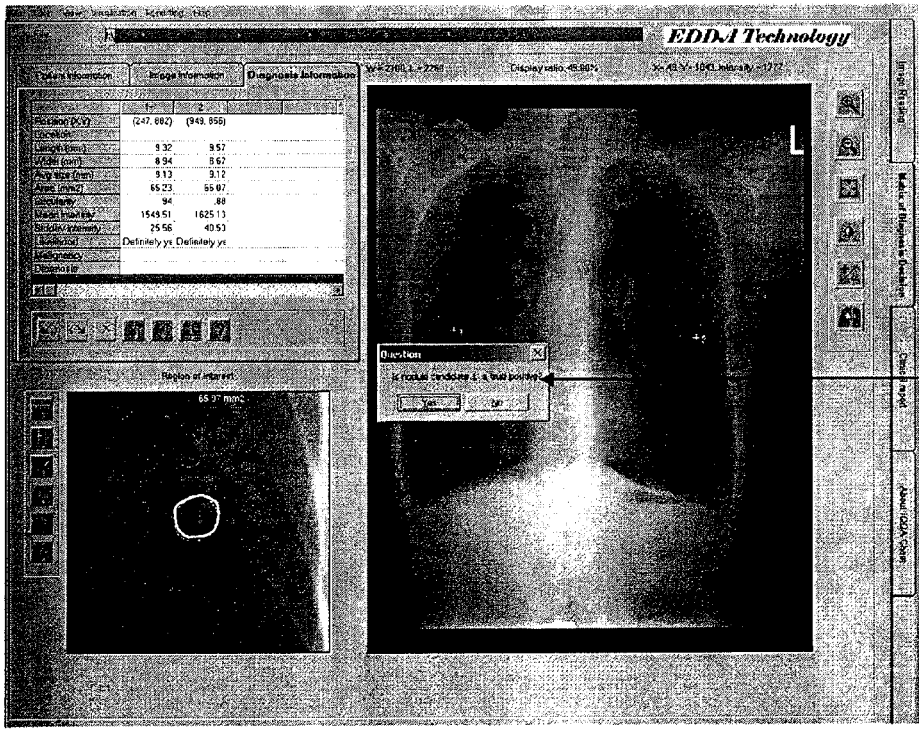
Figure 10C:
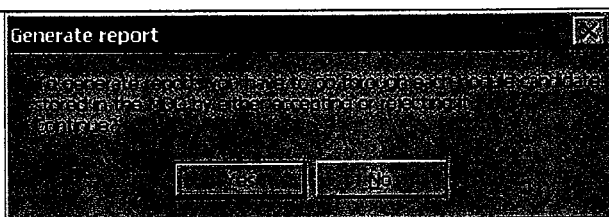
Figure 10D:
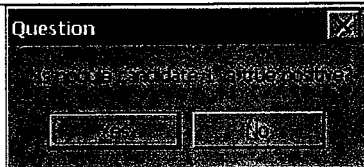

In operation, a user may have control of the workflow of the underlying system. Such control may be partial or full. With an adequate control, a user may utilize the system as a means to assist making a diagnostic decision. In addition to information and tools provided to assist diagnosis, other functions may also be provided. One example is to facilitate verification or confirmation processes for the nodules detected. As another example, the system may provide tools to produce a clinical report based on diagnostic activities and results. Different exemplary embodiments are shown in FIGS. 10(a)-10(d). In FIG. 10(a), a user is prompted via a pop-up dialog box 1002, after diagnosis is completed and prior to actually reporting the diagnosis results, to go through all the nodule candidates. In FIG. 10(b), a user is prompted via a dialog box 1004, for each detected nodule, to indicate whether the underlying nodule is to be reported. FIGS. 10(c) and 10(d) show enlarged views of the dialog boxes 1002 and 1004. In some embodiments, if information in the diagnosis information table is incomplete, a warning dialog box may be popped up to prompt a user to indicate whether the operation is to continue.

Figure 9A:
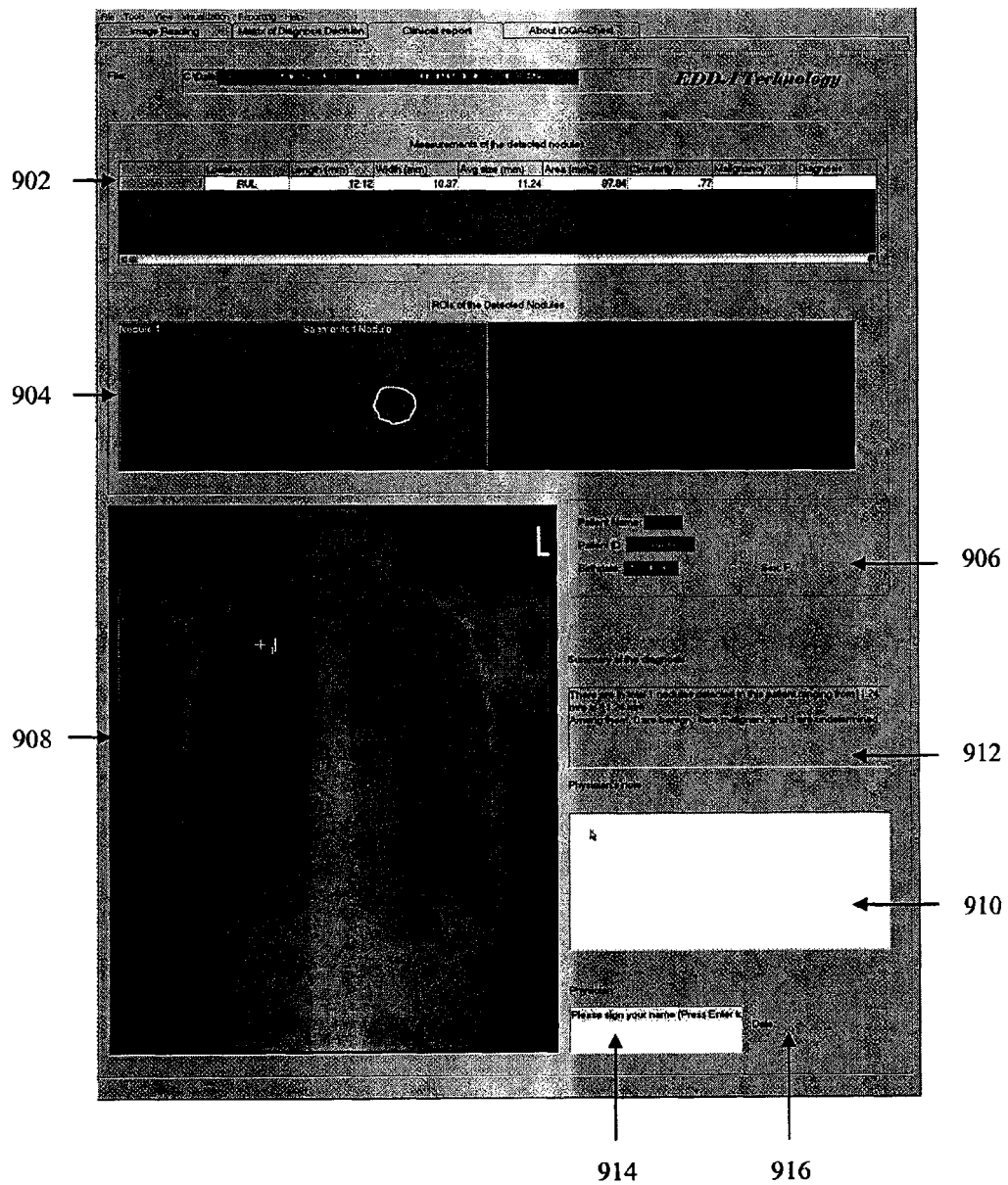
FIG. 9(a) shows an exemplary Clinical Reporting Platform displayed on a portrait monitor.
Figure 9B:
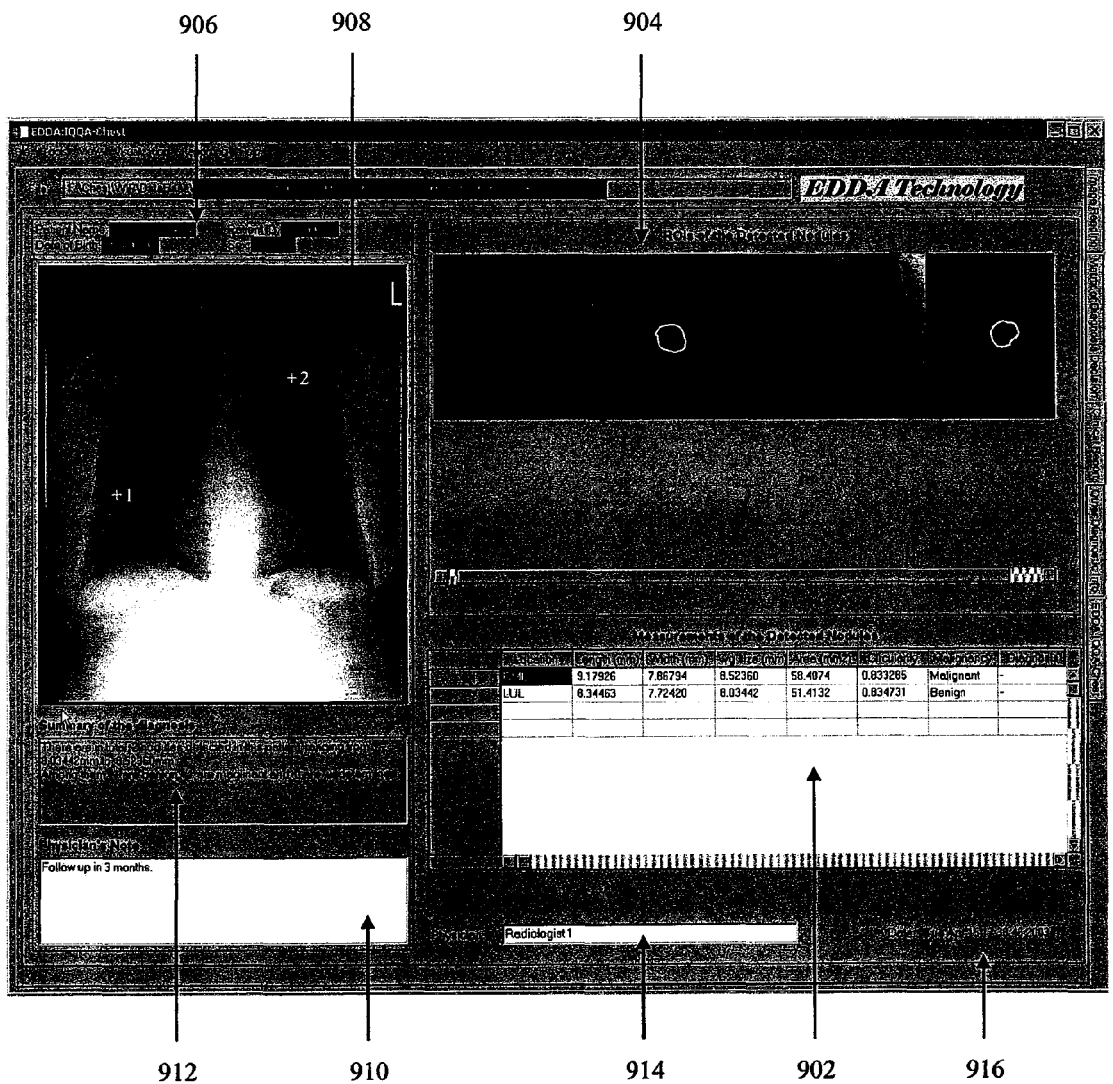
FIG. 9(b) shows an exemplary Clinical Reporting Platform displayed on a normal monitor.

In some embodiments, a user may select to automatically generate a clinical report according to recorded diagnostic relevant information. An automatically generated clinical report may comprise various types of information. Some types of the information included in a clinical report are illustrated in FIGS. 9(a) and 9(b), where the Clinical Reporting Platform may include an index image 908, general patient information 906, an examination summary 912, a treatment suggestion field 910 which may be filled by a user, regional images of abnormalities (ROIs) with segmentation results 904, corresponding quantitative measurements and qualitative characterizations 902 for the detected abnormalities, a name field 914 with a user's (e.g., a physician's) name, as well as a time field 916 with a date and time when the examination was performed. A user may enter appropriate information in corresponding fields such as the name of the physician who performs the diagnosis, date and time of the diagnosis, and suggestions as to, for example, treatment or further examination in the corresponding fields. The reporting time may also be entered or alternatively be automatically filled in by the underlying computer. Existence of a physician's name and report generating time may be provided as a measure of quality. The structure of such a generated report may be realized in a variety of different ways. For example, it may be realized as an XML document, a PDF document, a WORD document, a DICOM structured report, etc. A generated report may also be printed, stored, and loaded in the future.

In some embodiments, additional measures may be deployed to further assure the quality and/or security of a clinical report. For example, a clinical report may be encrypted to ensure privacy. A clinical report may also be stored using a certain naming convention so that a report associated with a patient is unique not only with respect to the patient but also with respect to each of the physicians who participated in the diagnosis decision. In some embodiments, reports generated for a patient by a physician at different times may be identified using a time identifier. An example of such a naming convention may be "patient name+patient ID+image ID+physician's name+time of the reporting+extension name". In some embodiments, mechanisms may be deployed to assure that only clinical reports associate with the current image may be loaded in for future review.

In some situations, a clinical report may be generated with respect to each type of imagery information such as a radiographic image. In other situations, a clinical report may be generated with respect to each nodule detected from a particular type of image. Each of such instances of clinical reports may be uniquely identified with respect to different physicians and difference times.

We hereby describe in detail methods running behind and supporting the system.

Spider Techniques

In some embodiments, nodule detection is realized using an algorithm that emulates a spider. In the physical world, a spider builds a web which is then utilized to capture insects. In some embodiments, a "Dynamic Live Spider" involves a set of algorithms configured to emulate a spider in the physical world. For example, a target object to be captured by the "Dynamic Live Spider" may be a nodule in a digital/digitized X-ray radiograph. The algorithms disclosed herein emulating a spider may be configured to detect or capture the presence of some defined target objects.

In some embodiments, a process of detecting and characterizing nodules may be described using an analogy to a process in nature where spider eggs mature into adult spiders, which then form webs that are used to catch food. In some embodiments, suspicious lesions may be automatically detected. In some situations, non-lesion regions that have similar visual appearance as a lesion may also be detected. Such detected regions, including ones containing actual lesions and ones that are not, may be considered as eggs of insects. In some embodiments, upon creating such eggs, an "incubation" process may be initiated, in which the eggs grow to become insects of possibly different species, each of which may have varying shapes and sizes corresponding to different anatomies and abnormalities present in an image. Following this incubation process, a natural selection process may begin, in which only spiders may be allowed to survive and other types of insects may be eliminated. Each of the surviving spiders may then be given opportunities to build a web to encompass a region of interest. Along a web, a spider may dynamically stretch its "sensors" along different threads of the web to capture what is caught on the web. In other words, evidence encountered along a web dynamically established from a surviving spider in an image may be detected, processed, and analyzed for diagnostic purposes. This stretching process may be initiated either from the center of a web outward or from the outside of a web inward towards the center of the web. Different image features and different ways of building webs may be applied based on application needs. In some embodiments, depending on whether the spider technique is applied to detect nodules or to segment nodules, a web may be built via different means and searching evidence along a web may be inward or outward.

Automatic Nodule Detection

In some embodiments, to automatically detect nodules, the disclosed spider technique may be used to emulate the process in which a living spider actively catches its target food. In some implementations, in applying the spider technique, a plurality of operational stages may be involved. For example, an initial stage may involve candidate generation and mutation, in which nodule candidates are generated as insect eggs. Such candidates may be localized and classified in a candidate location classification stage. Based on the classification results, nodules may be identified in a false positive removal stage.

Figure 11:
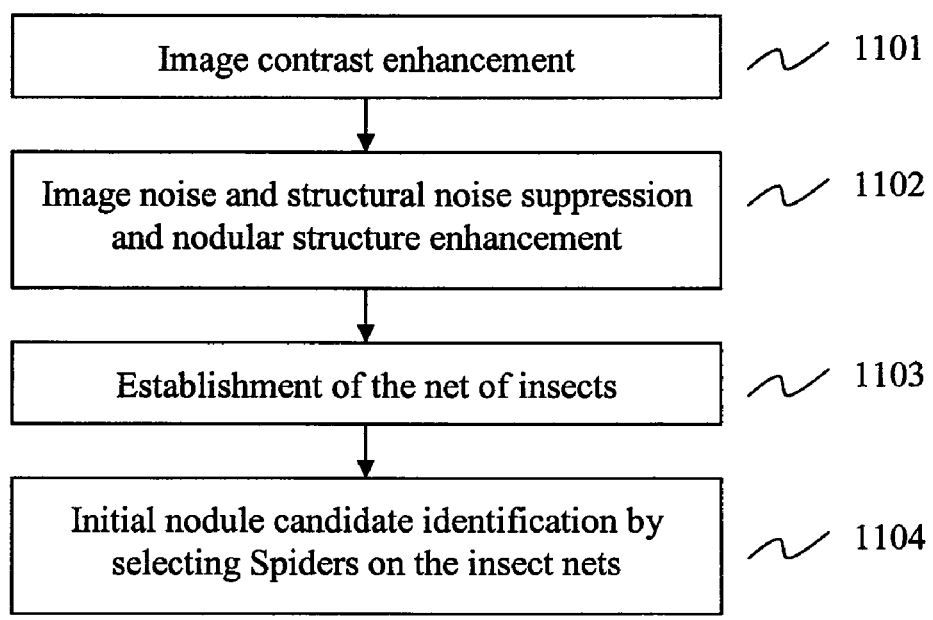
FIG. 11(a) is a flowchart of an exemplary process for identifying nodule candidates.
FIG. 11(b) is a flowchart of an exemplary process for removing false positive nodule candidates.
FIG. 11(c) is a flowchart of an exemplary process for removing false positive nodule candidates using Spider techniques.
Figure 12:
FIG. 12 shows exemplary net of insects.
Figure 13:
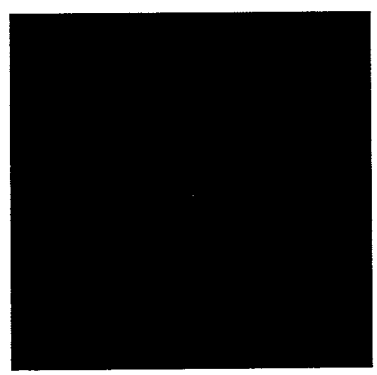
FIG. 13 shows an exemplary surviving spider during nodule candidate identification.

In some embodiments, initial nodule candidates may be generated based on analysis performed on a given image. For instance, analysis may be based on intensity distribution and shape patterns of detected nodules. In some situations, the visual features of a nodule may be characterized to have a local intensity peak with surrounding intensity valleys with an approximate round shape. Such characteristics may be observed from a digital or digitized radiographic image. FIG. 11(a) is a flowchart of an exemplary process, in which nodule candidates are identified. In this exemplary process, contrast of a given image may be enhanced at 1101 using, for example, wavelet transforms and manipulations. To suppress image noise and structural/anatomic noise and enhance nodular structures, a low-pass filter, such as a Laplacian of Gaussians (LoG), may be applied to a contrast enhanced image at 1102. A net of insects may be established by computing a topographic sketch of the image in one or more directions and then identifying regions, at 1103, that have crossing points of ridge lines and that are surrounded and separated by valley lines in the topographic sketch image. Such ridge and valley lines may, upon being put together, resemble a net of insects. An example of such a net of insects is illustrated in FIG. 12. In some embodiments, a topographic sketch may be derived along 4 directions: horizontal, vertical, and two diagonal directions. Based on the regions identified at 1103, the shapes of such regions may be analyzed and those regions that have an approximately round shape and of a proper size may be selected, at 1104, as initial nodule candidates. Such selected regions may have shapes similar to a spider. An example of a selected spider is shown in FIG. 13. Although similar in shape or in other features, such selected spider candidates may not correspond to actual nodules. This may be due to various reasons. For example, superimposing 3D anatomic structures onto a 2D image may produce undesirable structural noise in an image. In some embodiments, spider candidates generated may need to be further examined or classified.

In some exemplary process for lung nodule detection, nodule candidates may be classified into a plurality of categories according to, for example, information associated with the region where a detected nodule resides and the intensity characteristics of a detected nodule. For example, such categories may include a category classified based on intensity homogeneity of a detected nodule; a category classified based on contrast between a detected nodule and its nearby region; a category classified based on boundary strength of a detected nodule; and any combination thereof.

Figure 11B:
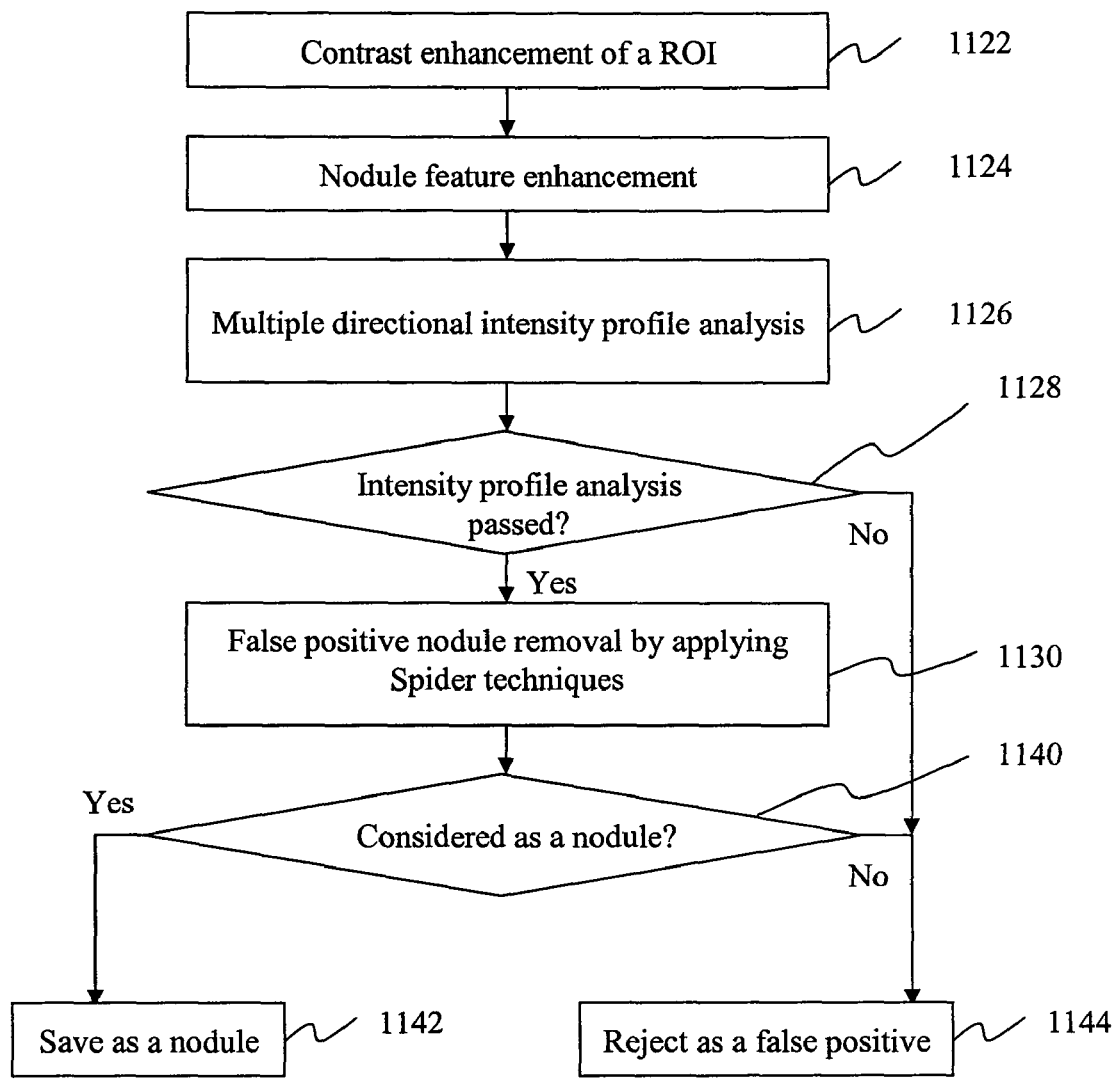

In some embodiments, for a nodule candidate in each classified category, another processing may be applied to remove false positive candidates. FIG. 11(b) is a flowchart of an exemplary process, in which false positive nodules may be removed, for example, from each region of interest.

In this exemplary process, contrast between a nodule candidate and its surrounding backgrounds may be enhanced at 1122. An exemplary enhancement technique may be wavelet-based enhancement. Features of the candidate nodule may be further enhanced. Inhomogeneity of the intensity distribution in an underlying ROI in which the nodule candidate resides may be compensated at 1124. In some embodiments, gray-scale morphological operations may be deployed for such purposes. The intensity profiles of an enhanced image in the ROI may be analyzed, at 1126, along, for example, multiple directions. If the profiles in multiple directions exhibit a particular distribution such as a Gaussian distribution around the nodule candidate and exhibit a certain degree of similarity, determined at 1128, the underlying nodule candidate may be further examined to see whether it is a false positive candidate at 1130. Otherwise, the nodule candidate may be classified at 1144 to be a false positive.

In some embodiments, to identify a false positive candidate, various types of information associated with likely features of a nodule may be utilized. For example, information about the homogeneity, brightness contrast, and boundary strength may be used when analyzing the intensity profiles (at 1126). Expected shape of a corresponding intensity profile may also be used in determining whether a nodule candidate corresponds to a false positive candidate. For nodule candidates that pass the intensity profile check (at 1128), further examination may be applied, at 1130, to remove false positive nodule candidates. In some implementations, the Spider technique may be applied to detect and remove false positive candidates. If a nodule candidate is classified as false positive, determined at 1140, it is rejected at 1144. Otherwise, it is stored as a detected nodule at 1142. Details related to applying the spider technique to identify a false positive candidate (at 1130) are discussed below.

Figure 11C:
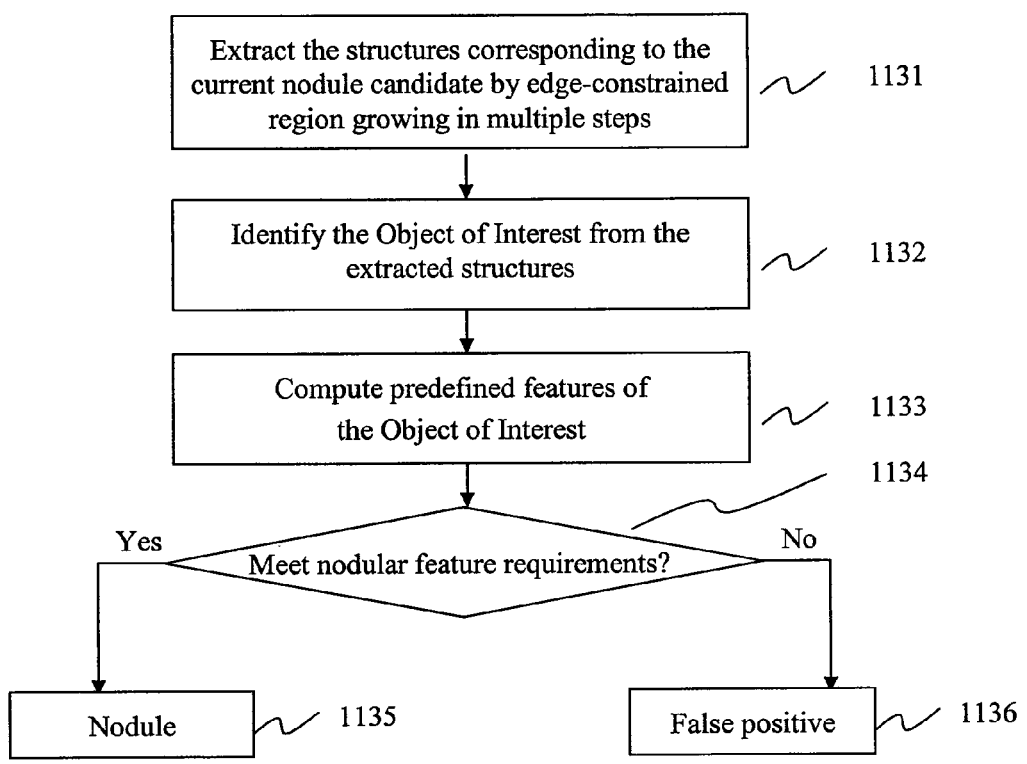
Figure 14A:
FIG. 14(a) shows an original region of interest in which a nodule attaches to bones.
Figure 14B:
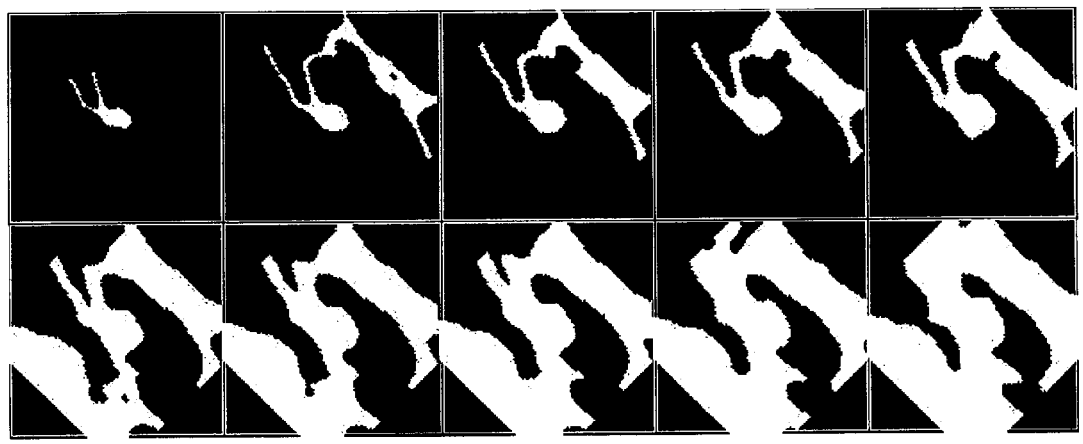
FIG. 14(b) illustrates a series of extracted objects corresponding to a nodule.

FIG. 11(c) illustrates an exemplary process of using the spider technique to remove false positive nodules. In this example, a suspicious nodule structure may be extracted at 1131. In some embodiments, this may be achieved by first performing edge detection within the region of interest to produce edge information. Then a plurality of subregions that correspond to the nodule structure may be extracted via, for example, edge constrained region growing where each of the region growing process may adopt a different threshold within the constraint of the detected edge information to obtain a different subregion as the growing result. In some embodiments, the growing may be initiated from an estimated center of a nodule candidate within a region of interest covering the nodule candidate. Boundaries of the subregions, as descriptors of the corresponding subregions, may form a spider web. This multiple step process may emulate a procedure according to which a spider builds and continuously extends a web. When there is weak intensity contrast between the nodule candidate and its surrounding structures, an extracted subregion may encompass both the target nodule and surrounding anatomical structures connected therewith. An example of a pulmonary nodule candidate connected to bones is illustrated in FIG. 14(a) where an arrow is pointing at the nodule candidate. In such described process, the lower and upper intensity thresholds may be relaxed in different scales so that different extraction results using different sets of threshold values may be derived. The amount of relaxation of the lower and upper thresholds at each step may be prefixed or may be dynamically adjusted. FIG. 14(b) illustrates exemplary subregions extracted in this multiple step process. They correspond to the nodule candidate illustrated in FIG. 14(a). In these exemplary results, the extracted subregions encompass not only the nodule region but also nearby anatomic structures such as bones.

In some embodiments, further analysis may be applied to a nodule region instead of an entire extracted subregion 1132. Such a nodule region may be smaller than an entire subregion.

To approximately identify the nodule region, a plurality of templates with various sizes are generated for each of the subregions. In some embodiments, each of the templates may center around a center of a nodule candidate and overlap with the underlying subregion. Such an overlap produces or yields an area of object of interest. In some embodiments, templates may be round with various sizes which may be pre-defined or may be dynamically computed. A template may also have a different shape such as oval with various sizes and orientations which may be pre-defined or dynamically computed. An area of object of interest may represent estimates of the nodule region.

Figure 15A:
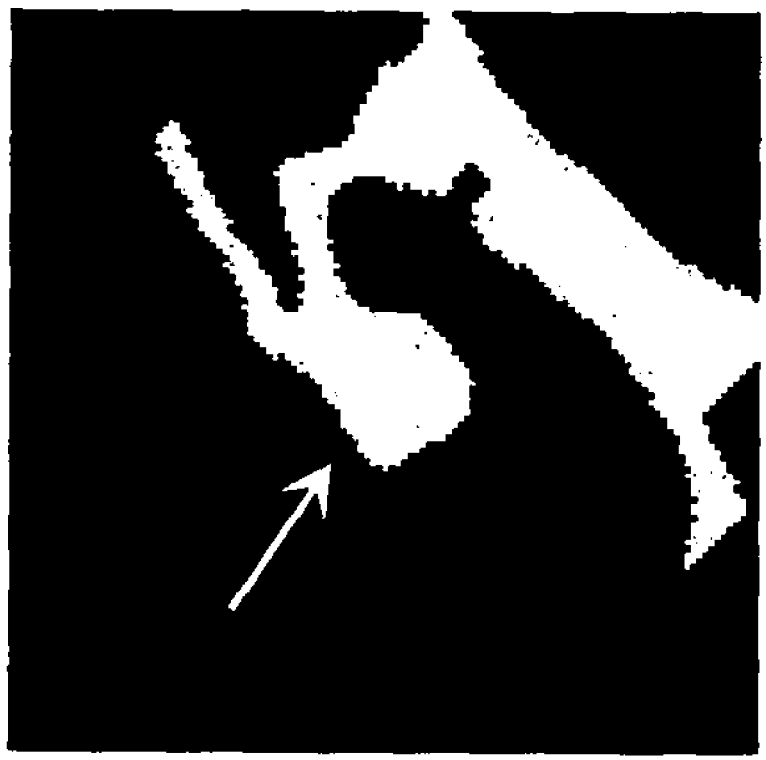
FIG. 15(a) illustrates an object extracted during the removal of false positive nodule candidates using Spider techniques.
Figure 15B:
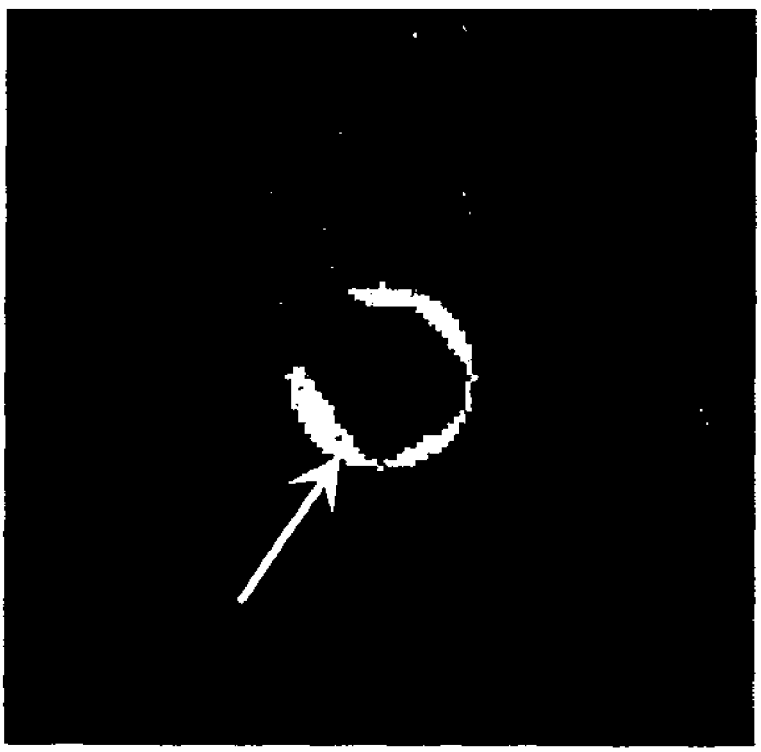
FIG. 15(b) shows an exemplary template that best captures a target nodule.

In some embodiments, certain features of an object of interest may be computed at 1133. Such features may include, but not limited to, size, circularity, boundary smoothness, an area measurement (for example, the ratio between the area of the object of interest OOI and the area of the template), ratio between the length of the part of the template boundary that intersects the extracted subregion and the perimeter of the template, edge strength along the boundary of an OOI, the difference of edge strength between the inner boundary and outer boundaries of an OOI, etc. A template that best captures the underlying nodule may be determined through examination of such features. Example of a subregion and a determined best template are illustrated in FIGS. 15(*a*) and 15(*b*), respectively. FIG. 15(*a*) shows an example of an extracted subregion containing both the nodule and bones and FIG. 15(*b*) shows an exemplary template identified to best capture the nodule using the features computed.

In some embodiments, a decision as to whether a nodule candidate is a false positive may be determined, at 1134, by analyzing the computed features in connection with utilizing knowledge-based reasoning. Such a process may emulate the process of a spider, on a web, sensing its target food described by certain features. For example, an actual nodule may be generally known to have an approximately round/oval shape, have a relatively higher occupation area, have small ratios between the lengths of the boundaries cutting the OOI from the whole extracted object and the perimeter of the template, and have relatively high edge strength along the boundaries of the OOI. In addition, a category of a nodule candidate may be utilized in the knowledge-based reasoning. For example, if a nodule shows strong inhomogeneous intensity distribution, it may suggest that the nodule is overlaid on a rib. Therefore, the effect of the rib edge in evaluating the edge strength along the OOI boundary may be taken into account. In addition to examining candidates in the intensity domain, intensity gradients and edges may also be analyzed along the web lines, for example, both in longitude and latitude directions. The features of the nodule candidate may include, but are not limited to, the magnitude and orientation of edges, their statistical distributions along web lines, such as the mean values and standard deviations, local and global spatial relationships of the strongest edges along the longitude lines. These features may be divided into groups according to their correlation strength and may be used as input to a set of cascaded classifiers to identify true nodules.

If a candidate is considered to be a nodule during the above reasoning process, the underlying candidate may be saved in a nodule list at 1135 and presented to the user for further examination. Otherwise, it is rejected as a false positive at 1136.

Lung Nodule Segmentation

Figure 16:
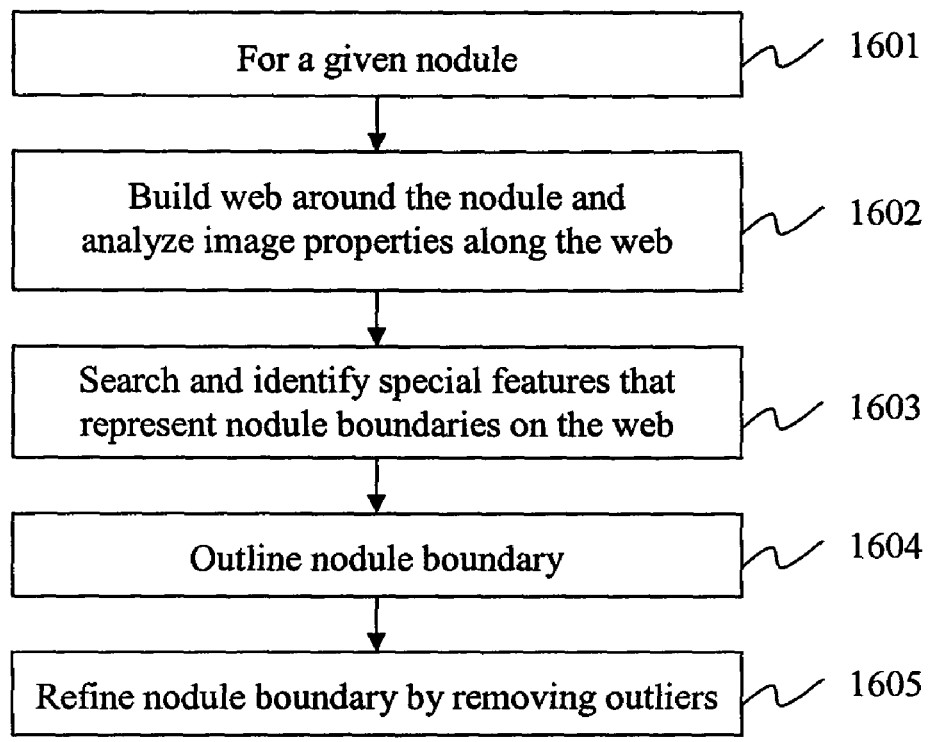
FIG. 16 shows an exemplary block diagram of Spider technique applied to nodule segmentation.

In some embodiments, the spider technique may be deployed in nodule segmentation. In some embodiments, such application of the spider technique may be implemented in real time processing. FIG. 16 is a flowchart of an exemplary process of nodule segmentation.

In this exemplary process, for a given nodule location, a spider may build a web in an area where the nodule resides. Local image properties may be analyzed at 1602 along the lines of the web. The web may be established using different means, including gridding or gridding with diagonal directions. By establishing a web, 2D processing may be reduced to 1D processing to reduce computational cost. Exemplary image properties to be analyzed may include intensity profile of the local image area, corresponding curvature of the intensity profile, curvature of a local histogram, edge strength, or a profile of a corresponding Laplacian of Gaussian (LoG) image.

Based on the local image properties, special features representing nodule boundaries may be identified at 1603 along the lines of the web. For example, by analyzing the intensity distribution in an nodule area, it may be recognized that although the intensity contrast along the boundary lines may be vague and the intensity distribution of nodules may vary, strong responses may still be generated around the nodule boundaries after certain processing such as applying a Laplacian of Gaussian (LoG) filter combined with edge enhancement filter, finding local maxima of the curvature of the local intensity profile, or applying a combination of both. Those positions where strong responses are identified may be consider to represent potential boundary positions of the nodule.

In some embodiments, to make segmentation more reliable and robust with respect to image noise and/or structural/anatomical noise, boundary points may be first roughly identified by finding local maxima on 1-D intensity profiles of an edge-enhanced and LoG-filtered image. This may make the segmentation less sensitive to image noise due to the fact that after applying an LoG filter, the effect of image noise and structures other than the nodule may be suppressed. However, the edge-enhanced and LoG-filtered images may be somehow distorted from the original images. Analysis of the local intensity profile curvatures of the original image and the edge enhanced image may be further applied to fine tune the segmentation. To do so, small search windows may be applied on 1-D profile curvature curves around the boundary points identified from the LoG intensity profiles, and the points of local maxima response with fair edge strength may be considered as the refined nodule boundary points.

In some embodiments, a segmented nodule may be outlined to derive its boundary at 1604, based on the nodule boundary points identified at 1603. The outlining operation may be performed based on vertices of a piece-wise-smooth polygon of the nodule boundary. The smoothness of the boundaries may be adjusted by configuring the denseness of the web lines.

Figure 17A:
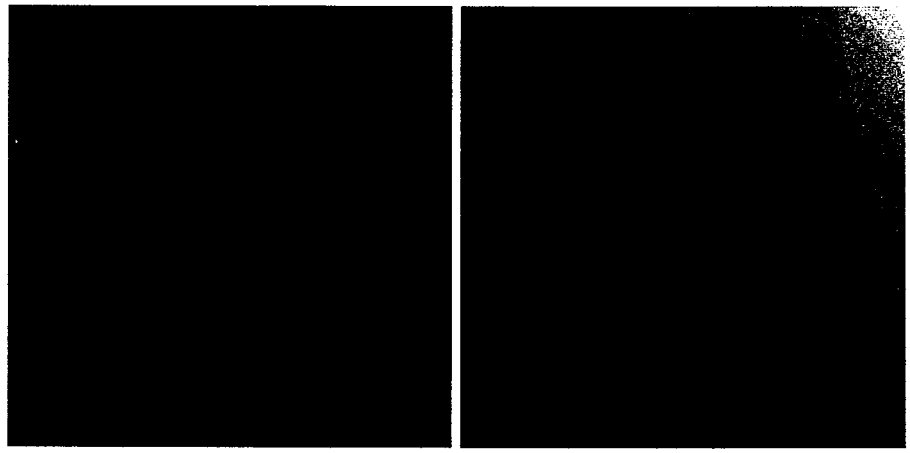
FIG. 17(a) illustrates two ROIs containing nodules.
Figure 17B:
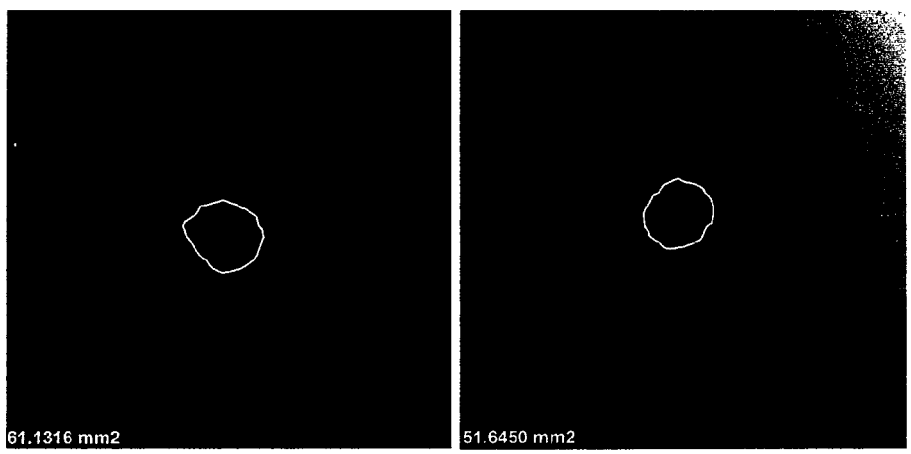
FIG. 17(b) illustrates examples of nodules segmented using Spider technique.

In some embodiments, determination of boundary points between vertices may be made in different ways. For example, local histograms around two adjacent vertices may be analyzed so that an optimal local intensity threshold can be chosen. It may also be achieved by an interpolation when, for example, vertices on the original boundary polygon are not adequately dense. In some situations, some of the identified boundary points may not be on the true boundary positions. In some embodiments, to solve this problem, neighboring boundary points may be utilized to refine, at 1605, the boundary by removing outliers according to, for example, a certain degree of predefined stiffness. FIG. 17(*a*) shows two example images each of which contain a nodule. FIG. 17(*b*) shows segmentation results derived from the two images in FIG. 17(*a*) using the spider technique.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method implemented on a machine having at least one processor, storage, and a communication platform, comprising:
    computing, by an image reading platform implemented on the at least one processor, a topographic image including a plurality of topographic sketches in a plurality of directions of an image,
    determining, by the image reading platform, a plurality of ridge lines and valley lines in the topographic image;
    locating, by the image reading platform, a region in the topographic image containing one or more crossing points of the plurality of determined ridge lines that are surrounded and/or separated by the plurality of determined valley lines;
    identifying, by the image reading platform, the located region as a nodule candidate when a geometric feature associated with the located region satisfies a certain condition; and
    performing, if one or more candidates are identified in the image, analysis to affirm or disaffirm the existence of the nodule of the pre-determined type with respect to each of the identified candidates based on information associated with the image.

2. The method according to claim 1, wherein the image includes a radiographic image.

3. The method according to claim 1, wherein the information associated with the image includes visual and non-visual information that is patient specific and/or disease specific or information computed from the image.

4. The method according to claim 1 further comprising:
    classifying the one or more identified candidates into a plurality of categories; and
    removing a candidate that is classified as a false target.

5. The method according to claim 4, wherein a category of a candidate includes at least one of:
    a category with a certain intensity homogeneity of the detected nodule;
    a category with a certain degree of contrast between the detected nodule and its nearby region;
    a category with a certain degree of edge strength along the boundary of the detected nodule; and
    any combination thereof.

6. The method according to claim 4, wherein said removing comprises:
    generating a first enhanced region of interest around each identified candidate to improve intensity contrast;
    generating a second enhanced region of interest based on the first enhanced region of interest to improve intensity homogeneity;
    determining whether the region of interest represents a false target based on intensity profile analysis of the second enhanced region of interest; and
    eliminating the region of interest if the region of interest is determined to be a false target.

7. The method according to claim 6, wherein said determining comprises:
    determining a center in the region of interest;
    performing edge detection within the region of interest to produce edge information;
    generating a plurality of subregions in the region of interest via edge constrained region growing from the center using a plurality of corresponding thresholds and based on the edge information;
    generating a plurality of templates for each of the subregions, wherein each of the templates centers around the center and overlaps with the underlying subregion yielding an object of interest;
    computing at least one feature for each object of interest;
    determining a best template from the plurality of templates based on the at least one feature computed for each object of interest wherein the best template captures the estimated nodule;
    determining whether the estimated nodule is an object of the pre-determined type; and
    classifying the region of interest as a false target if each estimated nodule from each subregion does not represent an object of the predetermined type.

8. The method according to claim 7, wherein each of the templates has a circular shape with a different radius around the center.

9. The method according to claim 7, wherein the at least one feature comprises at least one of:
    a size measure of an object of interest;
    a measure of circularity of an object of interest; a measure of boundary smoothness of an object of interest;
    an area measure of an object of interest;
    a length of a portion of the template boundary that intersects the underlying subregion;
    a perimeter of a template whose overlap with the underlying subregion yields the object of interest;
    a measure indicating strength of edge along the boundary of the object of interest; and
    a difference in edge strength between an inner boundary and an outer boundary of an object of interest.

10. The method according to claim 1 further comprising:
    enhancing the image to produce a first enhanced image; and
    filtering the first enhanced image to produce a filtered image, wherein
    the topographic image including the plurality of topographic sketches is computed in the plurality of directions of the filtered image.

11. The method according to claim 1, wherein the certain condition includes at least one of: a criterion related to a shape of the region; and a criterion related to a size of the region.

12. The method according to claim 11, wherein the criterion related to the shape of the region indicates that the region has a substantially round shape.

13. The method according to claim 11, wherein the criterion related to the size of the region indicates that the region has a size falling into a pre-defined range.

14. The method according to claim 1, further comprising reaching a medical decision based on the results from said analysis.

15. The method according to claim 14, wherein the medical decision is a diagnosis decision.

16. The method according to claim 1, further comprising automatically generating a report based on the results from said analysis and/or the medical decision and a user's confirmation.

17. The method according to claim 16, further comprising automatically summarizing the analysis results in the report.

18. A method implemented on a machine having at least one processor, storage, and a communication platform comprising:

computing, by an image reading platform implemented on the at least one processor, a topographic image including a plurality of topographic sketches in a plurality of directions of an image, determining, by the image reading platform, a plurality of ridge lines and valley lines in the topographic image;

locating, by the image reading platform, a region containing one or more crossing points of the plurality of determined ridge lines that are surrounded and/or separated by the plurality of determined valley lines;

identifying, by the image reading platform, the located region as a nodule candidate when a geometric feature associated with the located region satisfies a certain condition;

determining, by the image reading platform, an initial location in the identified candidate;

performing, by the image reading platform, edge detection within the identified candidate to produce edge information;

generating, by the image reading platform, a plurality of subregions in the identified candidate via edge constrained region growing from the initial location using a plurality of corresponding thresholds and based on the edge information;

generating, by the image reading platform, a plurality of templates for each of the subregions, wherein each of the templates centers around the initial location and overlaps with the underlying subregion yielding an area of object of interest;

computing, by the image reading platform, at least one feature for each area of object of interest; and selecting a best template from the plurality of templates based on the at least one feature computed for each area of object of interest.

19. The method according to claim 18, wherein each of the templates has a circular shape with a different radius around the initial location.

20. The method according to claim 18, wherein the at least one feature comprises at least one of:
   a size measure of an object of interest;
   a measure of circularity of an object of interest;
   a measure of boundary smoothness of an object of interest;
   an area measure of an object of interest;
   a length of a portion of the template boundary that intersects the underlying subregion;
   a perimeter of a template whose overlap with the underlying subregion yields the object of interest;
   a measure indicating strength of edge along the boundary of the object of interest; and
   a difference in edge strength between an inner boundary and an outer boundary of an object of interest.

21. The method according to claim 18, further comprising identifying whether the area of object of interest within the best template is an object of the pre-determined type.

22. The method according to claim 21, wherein said identifying comprises:
   computing a feature along a pre-defined direction within the area of object of interest; and
   determining whether the area of object of interest represents an object of the pre-determined type based on the computed feature.

23. A method implemented on a machine having at least one processor, storage, and a communication platform, comprising:
   computing, by an image reading platform implemented on the at least one processor, a topographic image including a plurality of topographic sketches in a plurality of directions of an image;
   determining, by the image reading platform, a plurality of ridge and valley lines in the topographic image;
   locating, by the image reading platform, a region in the topographic image containing one or more crossing points of the plurality of determined ridge lines that are surrounded and/or separated by the plurality of determined valley lines; and
   identifying, by the image reading platform, the region as a nodule candidate when at least one feature computed from the region satisfies a certain condition.

24. The method according to claim 23, wherein the certain condition includes at least one of: a criterion related to a shape of the region; and a criterion related to a size of the region.

25. The method according to claim 24, wherein the criterion related to the shape of the region indicates that the region has a substantially round shape.

26. The method according to claim 24, wherein the criterion related to the size of the region indicates that the region has a size falling into a pre-defined range.

27. The method according to claim 23, wherein the image is an enhanced image.

28. The method according to claim 23, wherein the image is a filtered image.

* * * * *